(12) United States Patent
O'Brien et al.

(10) Patent No.: US 8,334,340 B2
(45) Date of Patent: *Dec. 18, 2012

(54) SULFUR-CONTAINING CYCLOALIPHATIC COMPOUND, PROCESS FOR ITS PREPARATION, FILLED SULFUR-VULCANIZABLE ELASTOMER COMPOSITION CONTAINING SAME AND ARTICLES FABRICATED THEREFROM

(75) Inventors: Michael Joseph O'Brien, Clifton Park, NY (US); Robert James Perry, Niskayuna, NY (US); Richard W. Cruse, Yorktown Heights, NY (US); William Michael York, Concord, NC (US); Carla Recker, Hannover (DE); Thomas Kramer, Springe (DE); Katharina Herzog, Harsum (DE)

(73) Assignee: Momentive Performance Materials, Inc., Albany, NY (US)

( * ) Notice: Subject to any disclaimer, the term of this patent is extended or adjusted under 35 U.S.C. 154(b) by 799 days.

This patent is subject to a terminal disclaimer.

(21) Appl. No.: 12/290,366

(22) Filed: Oct. 30, 2008

(65) Prior Publication Data

US 2010/0113681 A1     May 6, 2010

(51) Int. Cl.
C08K 5/41       (2006.01)
C08C 19/20      (2006.01)
C07C 381/04     (2006.01)

(52) U.S. Cl. ........ 524/572; 524/571; 524/573; 524/574; 524/575; 525/332.6; 525/343; 525/344; 525/342; 525/353; 568/22; 568/26; 568/27; 568/28

(58) Field of Classification Search .................. 524/571, 524/572, 573, 574, 575; 525/332.6, 343, 525/344, 342, 353; 568/22, 26, 27, 28
See application file for complete search history.

(56) References Cited

U.S. PATENT DOCUMENTS

| | | | |
|---|---|---|---|
| 3,282,976 A | | 11/1966 | Dunbar |
| 3,284,481 A | | 11/1966 | Dunbar |
| 3,462,472 A | | 8/1969 | Dunbar et al. |
| 3,732,192 A | | 5/1973 | Arnold |
| 3,786,063 A | | 1/1974 | Arnold |
| 3,869,435 A | | 3/1975 | Trivette, Jr. |
| 4,417,012 A | * | 11/1983 | Moniotte .................. 524/83 |
| 4,508,865 A | | 4/1985 | Spivack et al. |
| 4,532,080 A | | 7/1985 | Delseth et al. |
| 4,810,812 A | | 3/1989 | Matsuda et al. |
| 5,342,900 A | | 8/1994 | Wolpers et al. |
| 6,809,146 B2 | | 10/2004 | Obrecht et al. |
| 6,841,653 B2 | | 1/2005 | Takahashi et al. |
| 2008/0161463 A1 | * | 7/2008 | Cruse et al. .................. 524/266 |

OTHER PUBLICATIONS

E. Vuorinen et al., "Amine carboxylates as vapour phase corrosion inhibitors", *British Corrosion Journal*, vol. 37:159-160 (2002).
A.I. Ahmed et al., "Inhibition of the acid corrosion of aluminium with some morpholine and thiosemicarbazide derivatives", *Anti-Corrosion*, vol. 35:4-8 (1988).
M.N. Desai et al., "Morpholine as a Corrosion Inhibitor for Aluminium Alloys in Hydrochloric Acid", *Brit. Corrosion J.*, vol. 4:315-317 (1969).
M.N. Desai et al., "Amines as Corrosion Inhibitors for Zinc in Hydrochloric Acid", *J. Appl. Phys.*, vol. 2:385-395 (1980).
A.A. Hafiz et al., "Ehanolamine morpholine oleate as corrosion inhibitor for mild steel in acid solutions", *Corrosion Engineering Science and Technology*, vol. 38:76-78 (2003).
M.M. Stefenel et al., "Corrosion Inhibition of Pure Aluminum by Morpholine-Methylene—Phosphonic Acid in Neutral Chloride Solution", *Corrosion*, vol. 57:898-904 (2001).
N.N. Gorilenko et al., "Influence of Morpholine Derivatives on Biogenic Sulfide Corrosion of Steel", *Protection of Metals*, vol. 22:393-395 (1986).
K. Ravichandran et al., Mannich Base Derivatives—A Novel Class of Corrosion Inhibitors for Cooling Water Systems, *Corros. Rev.*, vol. 19:29-42 (2001).
M.L. Zheludkevich et al., "Triazole and thiazole derivatives as corrosion inhibitors for AA2024 aluminium alloy", *Corr. Sci.*, vol. 47:3368-3383 (2005).
S. Ramesh et al., "Corrosion inhibition of mild steel in neutral aqueous solution by new triazole derivatives", *Electrochimica Acta*, vol. 49:811-820 (2004).
G. Brunoro et al., "Organic films for protection of copper and bronze against acid rain corrosion", *Corr. Sci.*, vol. 45:2219-2231 (2003).
W. Qafsaoui et al.,"Study of different triazole derivative inhibitors to protect cooper against pitting corrosion", *Journal of Applied Electrochemistry*, vol. 30:959-966 (2000).

* cited by examiner

*Primary Examiner* — Roberto Rabago
(74) *Attorney, Agent, or Firm* — Dominick G. Vicari; Joseph S. Ostroff

(57) ABSTRACT

A sulfur-containing cycloaliphatic compound, useful as a crosslinker for filled sulfur-vulcanizable elastomer compositions, is represented by the general formula:

$$G[-C_aH_{2a}-S-S(=O)_b-R]_n$$

wherein G is a saturated, monocyclic aliphatic group of valence n containing from 5 to 12 carbon atoms and optionally containing at least one halogen or a saturated monocyclic silicone $[RSiO-]_n[R_2SiO-]_p$ group of valence n; each R independently is a monovalent hydrocarbon of up to 20 carbon atoms; each occurrence of subscripts a and b independently is an integer wherein a is 2 to 6 and b is 1 or 2; n is an integer of from 3 to 6; and p is an integer of from 0 to 3.

18 Claims, No Drawings

SULFUR-CONTAINING CYCLOALIPHATIC COMPOUND, PROCESS FOR ITS PREPARATION, FILLED SULFUR-VULCANIZABLE ELASTOMER COMPOSITION CONTAINING SAME AND ARTICLES FABRICATED THEREFROM

FIELD OF THE INVENTION

The present invention relates to organosulfur compounds, processes for their preparation, filled sulfur-vulcanizable compositions containing organosulfur compounds as crosslinkers (vulcanizing agents) and articles such as tires, tire tread, weather stripping, hose, belts, seals, gaskets, shoe soles, and the like, fabricated from such compositions.

DESCRIPTION OF THE RELATED ART

Elemental sulfur is commonly used as a vulcanizing agent for unsaturated diene elastomers (rubbers). The crosslinks formed with sulfur are primarily polysulfidic crosslinks that increase the thermal stability of the elastomer vulcanizates.

The use of organic compounds possessing sulfur-containing reactive groups as vulcanizing agents for diene rubbers is known. These organosulfur compounds often contain only two dithiocarbamate or thiosulfonate groups chemically bonded to a bridging group. The low number of tie points provided by such compounds results in inadequate crosslinking of diene rubbers thus failing to achieve vulcanizates exhibiting a satisfactory balance of wear, traction and rolling resistance. In instances where more than two dithiocarbamate or thiosulfonate groups are chemically bonded to a bridging group, the bridging group often contains unstable linkages such as ether or ester linkages or lacks the flexibility needed to dissipate energy that can propagate cracks when a crosslinked (cured) elastomer is subjected to mechanical stress.

It would be desirable to have a crosslinker for sulfur-vulcanizable elastomers that improves the wear properties of articles manufactured therefrom, e.g., weather stripping, hose, belts, seals, gaskets, shoe soles, tires and tire components, specifically, tear and abrasive wear, while maintaining hardness, lower tan delta values at temperatures above 40° C. and increased tan delta values at temperatures of from 5° C. to −15° C.

SUMMARY OF THE INVENTION

According to the invention, there is provided a sulfur-containing cycloaliphatic compound, and mixtures thereof, of the general formula:

$$G[-C_aH_{2a}-S-S(=O)_b-R]_n \quad (1)$$

wherein G is a saturated, monocyclic aliphatic group of valence n containing from 5 to 12 carbon atoms and optionally containing at least one halogen or a saturated monocyclic silicone $[RSiO-]_n[R_2SiO-]_p$ group of valence n; each R independently is a monovalent hydrocarbon of up to 20 carbon atoms; each occurrence of subscripts a and b independently is an integer wherein a is 2 to 6 and b is 1 or 2; n is an integer of from 3 to 6; and p is an integer of from 0 to 3.

Further, in accordance with the present invention, the foregoing sulfur-containing cycloaliphatic compound is prepared by the process which comprises:

a) reacting poly-alkenyl-substituted cycloalkane with thio-acid in the presence of a free-radical source to provide poly-thiocarboxylate-substituted alkylcycloalkane;

b) reacting poly-thiocarboxylate-substituted alkylcylcoalkane with deblocking agent to form free poly-mercaptan-functional alkylcycloalkane;

c) reacting free poly-mercaptan-functional alkylcycloalkane with halogenating agent to provide poly-sulfenyl halide-functional cycloalkane; and, d) reacting poly-sulfenyl halide-functional alkylcycloalkane with alkali metal salt represented by the formula, $R-S(=O)_b^-M^+$, wherein R is a monovalent hydrocarbon of up to 20 carbon atoms; $M^+$ is an alkali metal cation; and the subscript b is an integer 1 or 2, to yield the sulfur-containing cycloaliphatic compound.

According to another aspect of the present invention, a curable filled elastomer composition is provided which comprises:

(i) at least one sulfur-vulcanizable elastomer;
(ii) at least one particulate filler; and,
(iii) a crosslinking effective amount of, as crosslinker for sulfur-vulcanizable elastomer (i), at least one sulfur-containing cycloaliphatic compound of the general formula:

$$G[-C_aH_{2a}-S-S(=O)_b-R]_n \quad (1)$$

wherein G is a saturated, monocyclic aliphatic group of valence n containing from 5 to 12 carbon atoms and optionally containing at least one halogen or a saturated monocyclic silicone $[RSiO-]_n[R_2SiO-]_p$ group of valence n; each R independently is a monovalent hydrocarbon of up to 20 carbon atoms; each occurrence of subscripts a and b independently is an integer wherein a is 2 to 6 and b is 1 or 2; n is an integer of from 3 to 6; and, p is an interger of from 0 to 3.

According to still another aspect of the present invention, an article such as a tire or tire component such as tread, hose, belt, seal, gasket, and the like, is fabricated by molding a quantity of the foregoing curable filled elastomer composition into the shape of the desired article and thereafter curing the composition.

In the specification and claims herein, the following terms and expressions are to be understood as indicated.

The term "elastomer" is synonymous, and therefore interchangeable, with "rubber".

The expression "coupling agent" means an agent capable of establishing an effective chemical and/or physical bond between a vulcanizable elastomer and its filler. Effective coupling agents have functional groups capable of bonding physically and/or chemically with filler, for example, between a silicon atom of the coupling agent and the hydroxyl (OH) surface groups of the filler to form a surface-O—Si bond, e.g., a siloxane when the surface contains silanols as in the case of silica, and, for example, sulfur atoms which are capable of bonding physically and/or chemically with the elastomer as a result of vulcanization (curing).

The expression "filler" means a substance that is added to the elastomer to either extend the elastomer or to reinforce the elastomeric network. Reinforcing fillers are materials whose moduli are higher than the organic polymer of the elastomeric composition and are capable of absorbing stress from the organic polymer when the elastomer is strained. Fillers include fibers, particulates, and sheet-like structures and can be composed of inorganic materials such as silicates, silica, clays, ceramics, carbon, diatomaceous earth, and organic materials such as organic polymers. The filler can be essentially inert to the other ingredients with which it is admixed or it can be reactive therewith.

The expression "particulate filler" means a particle or grouping of particles that form aggregates or agglomerates. Particulate fillers that are useful herein can be essentially inert to coupling agents with which they are admixed, e.g., silane coupling agents, or they can be reactive therewith.

The term "carrier" means a porous polymer or high surface area filler that has a high adsorption or absorption capability and is capable of carrying up to 75 percent liquid ingredient while maintaining its free-flowing and dry properties. Useful carriers herein are essentially inert to liquids and are capable of releasing or deabsorbing liquids when added to the sulfur-vulcanizable elastomeric composition.

It will be understood that any numerical range recited herein includes all sub-ranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof

DETAILED DESCRIPTION OF THE INVENTION

The sulfur-containing cycloaliphatic compound of the invention is represented by the following general formula:

$$G[-C_aH_{2a}-S-S(=O)_b-R]_n \qquad (1)$$

wherein G is a saturated, monocyclic aliphatic group of valence n containing from 5 to 12 carbon atoms and optionally containing at least one halogen or a saturated monocyclic silicone $[RSiO-]_n[R_2SiO-]_p$ group of valence n; each R independently is a monovalent hydrocarbon of up to 20 carbon atoms; each occurrence of subscripts a and b independently is an integer wherein a is 2 to 6 and b is 1 or 2; n is an integer of from 3 to 6; and, p is an integer of from 0 to 3.

The expression "monovalent hydrocarbon group" means any hydrocarbon group from which one hydrogen atom has been removed and is inclusive of alkyl, alkenyl, alkynyl, cyclic alkyl, cyclic alkenyl, cyclic alkynyl, aryl, aralkyl and arenyl.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Representative non-limiting examples of saturated, monocyclic aliphatic groups G in the sulfur-containing cycloaliphatic compounds of the invention are trivalent, tetravalent and pentavalent cyclopentane, cyclohexane, cycloheptane, cyclooctane, cyclodecane and cyclododecane. It is to be understood that the attachment of the $-C_aH_{2a}-S-S(=O)_b-R$ groups occurs in either an axial or equatorial stereochemical configuration about cycloalkyl ring G. The sulfur-containing cycloaliphatic compounds herein also include mixtures of stereoisomers in which the positions of the $-C_aH_{2a}-S-S(=O)_b-R$ groups in any one stereoisomer can all be in the equatorial position, the axial position or both the equatorial and axial positions. It is preferred that a mixture of stereoisomers herein contain at least 50 weight percent of isomer in which all the $-C_aH_{2a}-S-S(=O)_b-R$ groups are in the equatorial position relative to cycloaliphatic group G, and more preferably contain at least 80, and most preferably at least 90, weight percent of said stereoisomer. The stereochemistry about the cycloalkyl ring G is usually determined in the preparation of the poly-alkenyl-substituted cycloalkane intermediate or reactant. For example, in preparing 1,2,4-trivinylcyclohexane from the thermal rearrangement of cis, trans, trans-1,5,9-cyclododecantriene, the reaction conditions can effect the stereochemistry about the cyclohexyl ring. Distillation of the polyalkenyl-substituted cycloalkane or other separation methods such as preparative liquid chromatography can also be used to obtain the desired ratio of stereochemical isomers.

Representative and non-limiting examples of monovalent hydrocarbon group R in the sulfur-containing cycloaliphatic compound of the invention are methyl, ethyl, propyl, isopropyl, butyl, 2-ethylhexyl, cyclohexyl, cyclopentyl, phenyl, benzyl, tolyl, xylyl, methylbenzyl, and the like.

The divalent linking group, $-C_aH_{2a}-$, between the thiosulfonato group and the cycloalkyl ring can be linear or branched. It is preferred that the $-C_aH_{2a}-$ group be linear with the thiosulfonato group being on the terminal position. Representative and non-limiting examples of the divalent linking group are methylene, ethylene, propylene, butylene and hexylene. Preferred linking groups are ethylene and propylene.

Representative and non-limiting examples of the sulfur-containing cycloaliphatic compounds of the invention include: methanethiosulfonic acid 2-[4,6-bis-(2-methanesulfonylsulfanyl-ethyl)-2,4,6-trimethyl-[1,3,5,2,4,6]trioxatrisilinan-2-yl]-ethyl ester; benzenethiosulfonic acid 2-[4,6-bis-(2-benzenesulfonylsulfanyl-ethyl)-2,4,6-trimethyl-[1,3,5,2,4,6]trioxatrisilinan-2-yl]-ethyl ester, toluenethiosulfonic acid 2-[4,6-bis-(2-toluenesulfonylsulfanyl-ethyl)-2,4,6-trimethyl-[1,3,5,2,4,6]trioxatrisilinan-2-yl]-ethyl ester, toluene-4-thiosulfonic acid S-{2-[bis-2,4-(2-toluene-4-sulfonylsulfanyl-ethyl)-cyclohexyl]-ethyl}ester, ethenethiosulfonic acid S-{2-[bis-2,4-(2-ethenesulfonylsulfanyl-ethyl)-cyclohexyl]-ethyl}ester, cyclohexanethiosulfonic acid S-{2-[bis-2,4-(2-cyclohexanesulfonylsulfanyl-ethyl)-cyclohexyl]-ethyl}ester, benzenethiosulfonic acid S-{2-[bis-2,4-(2-benzenesulfonylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, methanethiosulfonic acid S-{2-[bis-2,4-(2-methanesulfonylsulfanyl-ethyl)-2,4-dichloro-cyclohexyl]-ethyl}ester, methanethiosulfonic acid S-{2-[bis-2,4-(2-methanesulfonylsulfanyl-ethyl)-cyclopentyl]-ethyl}ester, methanethiosulfonic acid S-{2-[bis-2,4-(2-methanesulfonylsulfanyl-ethyl)-cycloheptyl]-ethyl}ester, methanethiosulfonic acid S-{2-[bis-2,4-(2-methanesulfonyl-sulfanyl-ethyl)-cyclododecyl]-ethyl}ester, toluene-4-thiosulfonic acid S-{2-[bis-2,4-(2-toluene-4-sulfonylsulfanyl-ethyl)-cyclooctyl]-ethyl}ester, toluene-4-thiosulfonic acid S-{2-[tris -2,4,6-(2-toluene-4-sulfonylsulfanyl-ethyl)-cyclooctyl]-ethyl}ester, toluene-4-thiosulfonic acid S-{2-[tetra-3,5,7, 9-(2-toluene-4-sulfonylsulfanyl-ethyl)-cyclodecyl]-ethyl}ester, toluene-4-thiosulfonic acid S-{3-[bis-2,4-(2-toluene-4-sulfonylsulfanyl-propyl)-cyclohexyl]-ethyl}ester, toluene-4-thiosulfonic acid S-{4-[bis-2,4-(2-toluene-4-sulfonylsulfanyl-ethyl)-cyclohexyl]-butyl}ester, toluene-4-thiosulfonic acid S-{6-[bis-2,4-(2-toluene-4-sulfonylsulfanyl-ethyl)-cyclohexyl]-hexyl}ester, toluene-4-thiosulfinic acid S-{2-[bis-2,4-(2-toluene-4-sulfinylsulfanyl-ethyl)-cyclohexyl]-ethyl}ester, methylthiosulfinic acid S-{2-[bis-2,4-(2-methylsulfinylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, a mixture comprising 80 weight percent of toluene-4-thiosulfonic acid S-{2-[cis,cis-bis-2,4-(2-toluene-4-sulfonylsulfanyl-ethyl)-cyclohexyl]-ethyl}ester and at least 5 weight percent of toluene-4-thiosulfonic acid S-{2-[cis,trans-bis-2,4-(2-toluene-4-sulfonylsulfanyl-ethyl)-cyclohexyl]-ethyl}ester, a mixture comprising of 85 weight percent of toluene-4-thiosulfonic acid S-{2-[cis,cis-bis-2,4-(2-toluene-4-sulfonylsulfanyl-ethyl)-cyclohexyl]-ethyl}ester and at least 5 weight percent of toluene-4-thiosulfonic acid S-{2-[trans,cis-bis-2,4-(2-toluene-4-sulfonylsulfanyl-ethyl)-cyclohexyl]-ethyl}ester and mixtures thereof.

Preferred sulfur-containing cycloaliphatic compounds herein include methanethiosulfonic acid S-{2-[bis-2,4-(2-methanesulfonylsulfanyl-ethyl)-cyclohexyl]-ethyl}ester, benzenethiosulfonic acid S-{2-[bis-2,4-(2-benzenesulfonyl-sulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, a mixture comprising of 80 weight percent of toluene-4-thiosulfonic acid S-{2-[cis,cis-bis-2,4-(2-toluene-4-sulfonylsulfanyl-ethyl)-cyclohexyl]-ethyl}ester and at least 5 weight percent of toluene-4-thiosulfonic acid S-{2-[cis,trans-bis-2,4-(2-toluene-4-sulfonylsulfanyl-ethyl)-cyclohexyl]-ethyl}ester, and a mixture comprising of 85 weight percent of toluene-4-thiosulfonic acid S-{2-[cis,cis-bis-2,4-(2-toluene-4-sulfonylsulfanyl-ethyl)-cyclohexyl]-ethyl}ester and at least 5 weight percent of toluene-4-thiosulfonic acid S-{2-[trans,cis-bis-2, 4-(2-toluene-4-sulfonylsulfanyl-ethyl)-cyclohexyl]-ethyl}ester.

The sulfur-containing cycloaliphatic compound of the invention can be prepared by the process which comprises:
e) reacting poly-alkenyl-substituted cycloalkane with thioacid in the presence of a free-radical source to provide poly-thiocarboxylate-substituted alkylcycloalkane;
f) reacting poly-thiocarboxylate-substituted alkylcylcoalkane with deblocking agent to form free poly-mercaptan-functional alkylcycloalkane;
g) reacting free poly-mercaptan-functional alkylcycloalkane with halogenating agent to provide poly-sulfenyl halide-functional alkylcycloalkane; and,
h) reacting poly-sulfenyl halide-functional alkylcycloalkane with alkali metal salt represented by the formula, R—S(=O)$_b$$^-$M$^+$, wherein R is a monovalent hydrocarbon of up to 20 carbon atoms; M$^+$ is a alkali metal cation; and the subscript b is 1 or 2, to yield the sulfur-containing cycloaliphatic compound.

The foregoing process for preparing the sulfur-containing cycloaliphatic compounds of the invention is illustrated by the chemical equations for reaction steps (a)-(d):

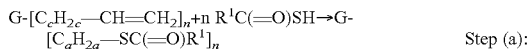   Step (a):

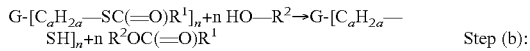   Step (b):

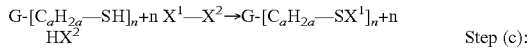   Step (c):

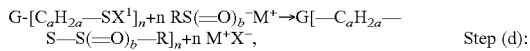   Step (d):

wherein:

G is a saturated, monocyclic aliphatic group of valence n containing from 5 to 12 carbon atoms and optionally containing at least one halogen or a saturated monocyclic silicone [RSiO—]$_n$[R$_2$SiO—]$_p$ group of valence n; each R independently is a monovalent hydrocarbon of up to 20 carbon atoms; each R$^1$ independently is a monovalent hydrocarbon of up to 20 carbon atoms; each R$^2$ independently is a monovalent hydrocarbon of up to 20 carbon atoms or M$^+$, wherein M$^+$ is an alkali metal cation; each occurrence of X$^1$ independently is a halogen atom selected from chlorine, bromine or iodine; each occurrence of X$^2$ independently is selected from X$^1$ and a succinimido group; each occurrence of subscripts a, b, and c independently is an integer wherein a is of from 2 to 6; b is 1 or 2; c is of from 0 to 4; n is an integer of from 3 to 6; and p is an integer of from 0 to 3.

The isomeric mixture of the sulfur-containing cycloaliphatic compounds is determined by the stereochemistry of the polyvalent cycloaliphatic compound containing three to five alkenyl groups, G-[C$_c$H$_{2c}$—CH=CH$_2$]n where G, c and n are defined above. The stereochemical structure of the reactants is not altered in the addition reaction of the thiocarboxylic acid group in step (a).

Trivinylcyclohexanes, which are the preferred starting materials for producing the sulfur-containing cycloaliphatic compounds of the present invention, can be formed by pyrolysis of 1,5,9-cyclododecatriene. The conversion of the 1,5,9-cyclododecatriene at elevated temperature, and optionally in the presence of a catalyst, results in the formation of the trivinylcyclohexane compound, as disclosed in U.S. Pat. No. 3,011,003 and British Patent No. 848,637, the entire contents of which are incorporated by reference herein.

The addition reaction of step (a) wherein the thiocarboxylic acid is reacted with a polyvalent cycloaliphatic compound containing three to five alkenyl groups, may optionally be carried out in the presence of a free radical reagent. Suitable free radical reagents include oxidizing agents that are capable of converting the thiocarboxylic acid to a thiocarboxylic acid radical, i.e., R$^1$C(=O)S●, and include, but are not limited to oxygen, peroxides, hydroperoxides, and the like, and UV radiation.

In the preparation of the G-[C$_a$H$_{2a}$—SC(=O)R$^1$]$_n$ intermediate, 0.95 to 3 molar equivalents, preferably 1.0 to 1.25 molar equivalents and most preferably a stoichimetric amount of thiocarboxylic acid, is used.

Effective amounts of peroxide or hydroperoxide free radical agent can range from 0.01 to 2, and preferably from 0.1 to 0.5, weight percent based upon the weight of the cycloaliphatic compound containing three to five alkenyl groups. When oxygen is used as the free radical generator, the source of the oxygen can be pure oxygen gas, air or a mixture of oxygen and an inert gas. Mixtures of oxygen and inert gas can contain from 3 to 15 weight percent oxygen with the balance being inert gas. Air or mixtures of oxygen and inert gas are generally preferred due to the difficulties in handling pure oxygen in the presence of organic materials and of these, air is preferred. The source of UV radiation can be a mercury lamp equipped with a quartz window.

Representative and non-limiting examples of cycloaliphatic compounds containing three to five alkenyl groups include 1,2,4-trivinylcyclohexane, 1,2,4-tripropenylcyclohexane, 1,3,5-trihexenylcyclohexane, 1,3,5,7-tetravinylcyclooctane, 1,3,5,7,9-pentavinylcyclodecane, and mixtures of at least 80 weight percent cis,cis,cis-1,2,4-trivinyl cyclohexane and at least 5 weight percent cis-trans-cis-1,2,4-trivinylcyclohexane.

Representative and non-limiting examples of thiocarboxylic acids include thioacetic acid, thiopropanoic acid, thiobutanoic acid, thiohexanoic acid, and the like.

Representative and non-limiting examples of peroxide and hydroperoxide free radical reagents include di(2,4-dichlorobenzoyl)peroxide, tert-butyl peroxypivalate, dilauroyl peroxide, dibenzoyl peroxide, tert-butyl peroxy-2-ethylhexanoate, 1,1-di(tert-butylperoxy)-3,3,5-trimethylcyclohexane, di(tert-butylperoxy)cyclohexane, tert-butyl peroxy-3,5,5-trimethylhexanoate, tert-butyl peroxyacetate, tert-butyl peroxybenzoate, di-tert-amyl peroxide, dicumyl peroxide, di(tert-butylperoxyisopropyl)benzene, 2,5-dimethyl-2,5-di(tert-butylperoxy)hexane, tert-butyl peroxyacetate, tert-butyl peroxybenzoate, di-tert-amyl peroxide, dicumyl peroxide, di(tert-butyl-peroxyisopropyl) benzene, 2,5-dimethyl-2,5-di(tert-butylperoxy)hexane, tert-butyl cumyl peroxide, 2,5-dimethyl-2,5-di(tert-butylperoxy) hexyne-3, di-tert-butyl peroxide, and the like.

The addition reaction of step (a) can be carried out at sub-ambient temperature, ambient temperature or elevated temperature, at sub-atmospheric, atmospheric or supra-atmospheric pressure and in the absence or presence of solvent. A suitable temperature range is from 0° C. to 200° C. and is preferably from 40° C. to 150° C. The reaction will ordinarily be run to completion. The time required to achieve this will depend upon the particular reaction conditions employed and whether a catalyst is used. Reaction times of from 5 minutes to 24 hours are usually suitable. Preferably, atmospheric pressure is used. Typical solvents include hydrocarbon solvents, including aromatic and aliphatic solvents, and chlorinated solvents.

The transesterification reaction of step (b) is effected by contacting the $G\text{-}[C_aH_{2a}\text{---}SC(\text{=}O)R^1]_n$ intermediate resulting from step (a) with an alcohol, optionally, in the presence of alkaline catalyst. The amount of alcohol can vary from stoichimetric to a large excess. Typically, from 1 to 20 equivalents of alcohol are used to affect the transesterification. Alternatively, the acyl group can be removed by saponification in the present of alkali metal hydroxide. Typical alkaline catalysts include lithium hydroxide, sodium hydroxide, potassium hydroxide, sodium methoxide, sodium ethoxide, potassium methoxide, potassium ethoxide, and the like.

The halogenation reaction of step (c) is effected by reacting the poly-mercapto-cycloaliphatic compound $G\text{-}[C_aH_{2a}\text{---}SH]_n$, resulting from step (b) with a halogen-containing oxidizing agent of the structure $X^1\text{---}X^2$ where G, $X^1$, $X^2$ and n are defined above. The halogenation reaction of step (c) can be carried out at sub-ambient temperature, ambient temperature or elevated temperature, at sub-atmospheric, atmospheric or supra-atmospheric pressure and in the absence or presence of solvent. The temperature of the reaction can range from −10° C. to 200° C. and is preferably within the range of from 0° C. to 50° C. The reaction will ordinarily be carried out to completion. Reaction times will vary depending upon the reaction condition utilized. Reaction times of from 5 minutes to 24 hours are generally suitable. Preferably, atmospheric pressure is employed in order to prevent the loss of halogenating reactant. Typical solvents include hydrocarbon solvents, including aromatic and aliphatic solvents, and halogenated solvents, including fluorinated and chlorinated solvents. Perhalogenated solvents, such as carbon tetrachloride are preferred to prevent reaction of the halogenating reactant with the solvent.

The reaction shown in step (d) can be carried out at sub-ambient temperature, ambient temperature or at elevated temperature, at sub-atmospheric, atmospheric or supra-atmospheric pressure and in the absence or presence of solvent. The preferred temperature range in from −15° C. to 100° C. It is also preferred to carry out the reaction in the presence of a solvent, in order to maintain a slurry of the reactants. Aprotic solvents such as aromatic and aliphatic solvent, chlorinated solvents and oxygenated solvent such as ethers, ketones and esters are preferred.

The sulfur-containing cycloaliphatic compound of the invention is particularly useful as a crosslinker for sulfur-vulcanizable elastomers (i). The sulfur-containing cycloaliphatic compound has from 3 to 5 reactive $\text{---}S\text{---}S(\text{=}O)_b\text{---}R$ groups, which are blocked mercaptans, that deblock during the curing reactions and generate a reactive mercaptan. The sulfur-containing cycloaliphatic compound therefore has three to five tie points to a rubber molecule. Although not wishing to be constrained by theory, it is believed that higher numbers of tie points, such as greater than 6, can result in a localized area in the bulk rubber that is very crowded and cannot effectively transfer stress, or energy, to the polymer chains or fillers. This transfer of stress is facilitated by the cycloaliphatic ring structure. The ring controls the average distance between the $\text{---}C_aH_{2a}S\text{---}S(\text{=}O)_b\text{---}R$ groups directing them outward from the ring. The orientation enables the reactive groups to attach to different polymer chains thereby improving the crosslinking efficiency. In addition, the cycloaliphatic ring is flexible, alternating between boat, chair and twist conformations. Under high stress, the ring is able to change to conformations that offer a pathway for absorbing energy. In the absence of this property, energy would be directed to bond scission resulting in poor wear and fatigue properties in the cured rubber composition. Linear and branched alkyl groups are not as effective at orienting the $\text{---}C_aH_{2a}S\text{---}S(\text{=}O)_b\text{---}R$ groups. Aromatic rings are planar and stiff and therefore cannot undergo these conformational changes. The preferred conformation about the cycloaliphatic ring, especially when the ring is a 1,2,4-substitutedcyclohexyl group, is the all -cis structure. The $\text{---}C_aH_{2a}\text{---}S(\text{=}O)_b\text{---}R$ groups at equilibrium are primarily in the equatorial position since when the conformation changes to the all-axial positions, it is the 1,3-steric interactions that occur. The all -cis structure orients the $\text{---}C_aH_{2a}S\text{---}S(\text{=}O)_b\text{---}R$ groups away from each other, maximizing the average distance between the $\text{---}C_aH_{2a}S\text{---}S(\text{=}O)_b\text{---}R$ groups.

The concentration of sulfur-vulcanizable elastomer(s) (i) in the curable filled elastomer composition herein can range from 10 to 99, preferably from 50 to 95, and more preferably from 60 to 85, weight percent of the entire weight of the composition.

The concentration of particulate filler (ii) in the curable filled elastomer composition of the invention can range from 0.5 to 90, preferably from 5 to 60, and more preferably from 10 to 50, weight percent of the entire weight of the composition.

The concentration of crosslinking sulfur-containing cycloaliphatic compound (iii) of the invention in the filled sulfur-vulcanizable elastomer composition can range from 0.05 to 30, preferably from 0.5 to 10, and more preferably from 2 to 5, weight percent of the entire weight of the composition.

Fillers can be used as carriers for liquid sulfur-containing cycloaliphatic compounds. Fillers that are used as carriers should be non-reactive with sulfur-containing cycloaliphatic compounds. The non-reactive nature of such fillers will be demonstrated by the ability of a sulfur-containing cycloaliphatic compound to be extracted from the filler at greater than 50 percent of its original loading therein using an organic solvent. The extraction procedure is described in U.S. Pat. No. 6,005,027, the entire contents of which are incorporated by reference herein. Fillers and carriers include, but are not limited to, porous organic polymers, carbon black, diatomaceous earth, and silicas.

Reinforcing fillers useful in the present invention include fillers in which the silanes are reactive with the surface of the filler. Representative examples of such fillers include, but are not limited to, siliceous fillers, metal oxides such as silica (pyrogenic and/or precipitated), titanium, aluminosilicate and alumina, clays, talc, and the like. The fillers may be provided in the hydrated form. Particulate, precipitated silica is especially useful as filler, particularly when the silica has reactive surface silanols.

The porosity of a filler can be determined, e.g., by the known technique of mercury porosimetry. In accordance with this method, the pores of a filler are penetrated with mercury after a thermal treatment to remove volatiles. Test conditions utilize a 100 mg sample and the removal of volatiles over 2 hours at 105° C. and ambient to 2000 bars pressure. Mercury porosimetry may be performed according to the method described by Winslow et al. in ASTM bulletin, p. 39 (1959) or according to DIN 66133. For the measurement, a CARLO-ERBA Porosimeter 2000 may be used. The average mercury porosity specific surface area for a silica filler herein should range from 100 to 300 m$^2$/g.

The pore size distribution for a preferred silica, alumina or aluminosilicate filler according to such mercury porosity measurement is considered herein to be such that five percent or less of its pores have a diameter of less than 10 nm, 60 to 90 percent of its pores have a diameter of 10 to 100 nm, 10 to 30 percent of its pores have a diameter at 100 to 1,000 nm and 5 to 20 percent of its pores have a diameter of greater than 1,000 nm.

Suitable silica fillers include those having an average particle size, e.g., in the range of from 10 to 50 nm as determined by electron microscopy, although smaller and larger particle sizes are also useful. Various commercially available silicas that are suitable for use herein include, e.g., those from PPG Industries such as HI-SIL 210 and HI-SIL 243, etc.; those from Rhone-Poulenc such as ZEOSIL 1165MP; those from Degussa such as VN2 and VN3, etc., and those from Huber such as HUBERSIL 8745.

In one embodiment, one or more fillers are combined with silane coupling agent. The filler can be a mixture of siliceous filler such as silica, alumina and/or aluminosilicate and a carbon black reinforcing pigment. Thus, the filler component can be a mixture of from 15 to 95 weight percent of siliceous filler with the balance being carbon black, e.g., one having a CTAB value of from 80 to 150, and can contain from 0.1 to 20 weight percent of a silane coupling agent, including, illustratively, one or more of 3-mercaptopropyltriethoxysilane, bis-(3-triethoxysilylpropyl) tetrasulfide, bis-(3-triethoxysilylpropyl)disulfide, S-thiooctanonic acid, 3-triethoxysilylpropyl ester, and a silylated core polysulfide, the structures of which are disclosed in U.S. published patent applications 2008/0161461 and 2008/0161477, the entire contents of which are incorporated by reference herein. In another embodiment, the weight ratio of siliceous filler to carbon black is at least 3 to 1, preferably at least 10 to 1 and more preferably at least 30 to 1.

Filler mixtures can contain from 60 to 95 weight percent of silica, alumina and/or aluminosilicate and, correspondingly, from 40 to 5 weight percent carbon black, and from 0.1 to 20 weight percent silane coupling agent, with the proviso that the mixture of the components add up to 100 percent. The siliceous filler and carbon black may be pre-blended or blended together in the manufacture of the vulcanized rubber.

Sulfur-vulcanizable elastomers (i) herein include conjugated diene homopolymers and copolymers and copolymers of at least one conjugated diene and aromatic vinyl compound. Suitable organic polymers for preparation of rubber compositions are well known in the art and are described in various textbooks including "The Vanderbilt Rubber Handbook," Ohm, R. F., R. T. Vanderbilt Company, Inc., 1990 and in the "Manual for the Rubber Industry," Kemperman, T. and Koch, S. Jr., Bayer A G, LeverKusen, 1993.

In one embodiment of the present invention, the sulfur-vulcanizable elastomer is solution-prepared styrene-butadiene rubber (SSBR), e.g., one having a styrene content of from 5 to 50, and preferably from 9 to 36, percent. In other embodiments of the present invention, the sulfur-vulcanizable elastomer is selected from the group consisting of emulsion-prepared styrene-butadiene rubber (ESBR), natural rubber (NR), ethylene-propylene copolymers and terpolymers (EP, EPDM), acrylonitrile-butadiene rubber (NBR), polybutadiene (BR), and the like, and mixtures thereof Suitable conjugated diene elastomers include, but are not limited to, isoprene and 1,3-butadiene and suitable vinyl aromatic elastomers include, but are not limited to, styrene and alpha methyl styrene. Useful polybutadienes include those typically containing about 90 percent by weight of the units in the cis-1,4-butadiene form.

The sulfur-vulcanizable elastomer (i) may be selected, e.g., from at least one of cis-1,4-polyisoprene rubber (natural and/or synthetic), emulsion polymerization-prepared styrene/butadiene copolymer rubber, organic solution polymerization-prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization-prepared styrene/butadiene/acrylonitrile terpolymer rubber and butadiene/acrylonitrile copolymer rubber. For some applications, an emulsion polymerization-prepared styrene/butadiene (ESBR) having a relatively conventional styrene content of from 20 to 28 percent bound styrene, or an ESBR having a medium to relatively high bound styrene content of from 30 to 45 percent, may be used.

Emulsion polymerization-prepared styrene/butadiene/acrylonitrile terpolymer rubbers containing from 2 to 40 weight percent bound acrylonitrile in the terpolymer are also contemplated as diene based rubbers for use in this invention.

The cured, i.e., vulcanized, elastomer composition herein contains a sufficient amount of filler(s) (ii) as to exhibit a reasonably high modulus, as for example a modulus at 100 percent strain of greater than 8 MPa, and high resistance to tear, as for example, a tear strength of greater than 25 N. In one embodiment of the present invention, the combined weight of the filler may be as low as 5 to 100 parts per hundred parts (phr). In another embodiment, the combined weight of the filler is from 25 to 85 phr and at least one precipitated silica is utilized as a filler in another embodiment. The silica may be characterized as having a BET surface area, as measured using nitrogen gas, from 40 to 600, and preferably from 50 to 300, $m^2/g$. The BET method of measuring surface area is described in the *Journal of the American Chemical Society*, Volume 60, page 304 (1930). The silica may also be characterized as having a dibutylphthalate (DBP) absorption value of from 100 to 350, and preferably of from 150 to 300. Further, the silica, as well as the aforesaid alumina and aluminosilicate, may have a CTAB surface area of from 100 to 220. CTAB surface area is the external surface area as determined with cetyl trimethylammonium bromide with a pH of about 9. The method is described in ASTM D 3849.

In practice, a vulcanized elastomer article is typically prepared by thermomechanically mixing the sulfur-vulcanizable elastomer(s) (i), filler(s) (ii) and sulfur-containing cycloaliphatic crosslinker(s) (iii) in a sequentially step-wise manner to provide a curable elastomer followed by molding and curing the compositions to provide the article. First, for the aforesaid mixing of the sulfur-vulcanizable elastomer(s) and other components, typically exclusive of the sulfur-containing cycloaliphatic crosslinker, sulfur and sulfur vulcanization accelerators (collectively, curing agents), the elastomer (s) and various elastomer compounding ingredients typically are blended in at least one, and often (in the case of silica-filled low rolling resistance tires) two or more, preparatory thermomechanical mixing stage(s) in suitable mixers. Such preparatory mixing is referred to as nonproductive mixing or non-productive mixing steps or stages. Such preparatory mixing usually is conducted at temperatures of from 140° C. to 200° C., and for some compositions from 150° C. to 170° C. Subsequent to such preparatory mix stages, in a final mixing stage, sometimes referred to as a productive mixing stage, curing agents, and possibly one or more additional ingredients, are mixed with the rubber compound or composition at lower temperatures, e.g., from 50° C. to 130° C., in order to prevent or retard premature curing of the sulfur-vulcanizable rubber, sometimes referred to as scorching. The rubber mixture, also referred to as a rubber compound or composition, typically is allowed to cool, sometimes after or during a process of intermediate mill mixing, between the aforesaid various mixing steps, for example, to a temperature of about 50° C. or lower. When it is desired to mold and cure a filled curable elastomer composition, the desired quantity of the composition is introduced into a mold of appropriate configuration and at a temperature of from 130° C. to 200° C., vulcanization of the rubber is achieved through reaction with the sulfur-containing groups of the sulfur-containing cycloaliphatic crosslinker herein and any other sources of free sulfur that may be present in the composition.

Thermomechanical mixing refers to the phenomenon whereby under the high shear conditions in a rubber mixer, the shear forces and associated friction occurring as a result of mixing the rubber compound, or some blend of the rubber compound itself and rubber compounding ingredients in the high shear mixer, the temperature autogeneously increases, i.e., it "heats up". Several chemical reactions may occur at various steps in the mixing and curing processes.

One or more other sulfur sources may be used, for example, in the form of elemental sulfur such as, but not limited to, $S_8$. A sulfur donor is considered herein to be a sulfur-containing compound which liberates free, or elemental, sulfur at a temperature in the range of from 140° C. to 190° C. Such sulfur donors include polysulfide vulcanization accelerators and organosilane polysulfides with at least two connecting sulfur atoms in their polysulfide bridges. The amount of free sulfur source in the curable composition herein can be controlled or adjusted as a matter of choice relatively independently of the addition of the sulfur-containing cycloaliphatic crosslinker.

In one embodiment of the invention, the rubber composition can comprise 100 parts by weight rubber (phr) of at least one sulfur-vulcanizable rubber selected from the group consisting of conjugated diene homopolymers and copolymers, and copolymers of at least one conjugated diene and aromatic vinyl compound, from 5 to 100 phr, and preferably from 25 to 80 phr, of at least one filler, up to 5 phr curing agent, and from 0.05 to 25 phr of at least one sulfur-containing cycloaliphatic compound of the present invention as crosslinker.

In another embodiment, the filler composition can comprise from 1 to 85 weight percent carbon black based on the total weight of the filler composition and from 0.5 to 10 parts by weight of at least one sulfur-containing cycloaliphatic compound of the present invention as crosslinker based on the total weight of the rubber composition.

The rubber composition can be prepared by first blending rubber, filler and silane coupling agent, or rubber and filler pretreated with all or a portion of the silane coupling agent, if needed, in a first thermomechanical mixing step to a temperature of from 120° C. to 200° C. for from 2 to 20 minutes. The sulfur-containing cycloaliphatic crosslinker and other curing agent(s), if present, are then added in a subsequent thermomechanical mixing step at a temperature of from 50° C. to 100° C. for 1 to 30 minutes. The temperature is then increased to from 130° C. to 200° C. with curing being accomplished in from 5 to 60 minutes.

In another embodiment of the present invention, the process may also comprise the additional steps of preparing an assembly of a tire or sulfur-vulcanizable rubber with a tread comprised of the rubber composition prepared according to this invention and vulcanizing the assembly at a temperature in the range of from 130° C. to 200° C.

Other optional ingredients may be added in the rubber compositions of the present invention including coupling agents, e.g., silane coupling agents, curing aids, e.g., sulfur compounds, including activators, retarders and accelerators, processing additives such as oils, plasticizers, tacking resins, silicas, other fillers, pigments, fatty acids, zinc oxide, waxes, antioxidants and antiozonants, peptizing agents, reinforcing materials such as, for example, carbon black, and so forth. Such additives are selected based upon the intended use and on the sulfur vulcanizable material selected for use, and such selection is within the knowledge of one of skill in the art, as are the required amounts of such additives known to one of skill in the art.

The vulcanization may be conducted in the presence of additional sulfur vulcanizing agents. Examples of suitable sulfur vulcanizing agents include, for example elemental sulfur (free sulfur) or sulfur-donating vulcanizing agents, for example, an amino disulfide, polymeric polysulfide or sulfur olefin adducts which are conventionally added in the final, productive, rubber composition mixing step. The sulfur vulcanizing agents, which are common in the art are used, or added in the productive mixing stage, in an amount ranging from 0.4 to 3 phr, or even in some circumstances up to 8 phr, with a range of from 1.5 to 2.5 phr in one embodiment and from 2 to 2.5 phr in another embodiment.

Vulcanization accelerators, i.e., additional sulfur donors, may be used herein, e.g., benzothiazoles, alkyl thiuram disulfides, guanidine derivatives and thiocarbamates. Specific representatives of these accelerators include mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other sulfur donors include, e.g., thiuram and morpholine derivatives. Specific representatives of such donors include dimorpholine disulfide, dimorpholine tetrasulfide, tetramethyl thiuram tetrasulfide, benzothiazyl-2,N-dithiomorpholide, thioplasts, dipentamethylenethiuram hexasulfide and disulfidecaprolactam.

Accelerators are used to control the time and/or temperature required for vulcanization and to improve the properties of the vulcanizate. In one embodiment, a single accelerator system may be used, i.e., a primary accelerator. Conventionally, a primary accelerator is used in total amounts ranging from 0.5 to 4, and preferably from 0.8 to 1. 5, phr. Combinations of primary and a secondary accelerators can also be used with the secondary accelerator being present in smaller amounts, e.g., from 0.05 to about 3 phr, in order to activate and to improve the properties of the vulcanizate. Delayed action accelerators and/or vulcanization retarders may also be used. Suitable types of accelerators are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator can be a guanidine, dithiocarbamate or thiuram compound.

Typical amounts of tackifier resins, if used, are from 0.5 to 10 phr, and preferably from 1 to 5 phr. Typical amounts of processing aids are 1 to 50 phr. Suitable processing aids include, e.g., aromatic, naphthenic and/or paraffinic processing oils. Typical amounts of antioxidants are from 1 to 5 phr. Representative antioxidants include diphenyl-p-phenylenediamine and others, such as, for example, those identified in the "Vanderbilt Rubber Handbook" (1978), pages 344-346. Typical amounts of antiozonants are from 1 to 5 phr. Typical amounts of fatty acids, e.g., stearic acid, if used are from 0.5 to 3 phr. Typical amounts of zinc oxide are from 2 to 5 phr. Typical amounts of waxes, e.g., microcrystalline waxes, are from 1 to 5 phr. Typical amounts of peptizers, e.g., pentachlorothiophenol and dibenzamidodiphenyl disulfide, are from 0.1 to 1 phr.

The cured rubber compositions of this invention can be used for various purposes such as the manufacture of tires, weather stripping, hose, belts, seals, gaskets, shoe soles, and the like. In one embodiment of the present invention, the rubber compositions described herein are particularly useful for manufacturing tire treads but can be used for all other parts of a tire as well. The tires can be built, shaped, molded and cured by any of various methods which are well known to those skilled in the art.

The examples presented illustrate the synthesis of sulfur-containing cycloaliphatic compounds herein and their use as crosslinkers for filled sulfur-vulcanizable elastomer compositions.

EXAMPLE 1

This example illustrates the preparation of toluene-4-thiosulfonic acid S-{2-[bis-2,4-(2-toluene-4-sulfonylsulfanyl-ethyl)-cyclohexyl]-ethyl}ester whose structure is:

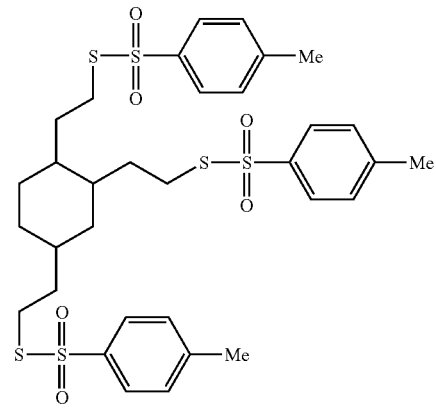

Thioacetic acid (1,974 grams, 25.9 mol.) was charged into a 5-liter round bottom flask. Air was bubbled into the thioacetic acid using a fritted tube. 1,2,4-Trivinylcyclohexane (1,303 grams, 8.0 mol.) was added dropwise using an addition funnel over a period of 2.5 hours. An exotherm was observed. The temperature was maintained at 32° C. using an ice bath. After 4 hours, the ice bath was removed and the reaction mixture was stirred for an additional 16 hours while air was bubbled through the reaction mixture. The excess thioacetic acid was removed by stripping the solution under vacuum at approximately 100° C. The yield was quantitative, producing 3,137 grams of product. GC analysis confirmed that the reaction was complete.

The acyl group was removed by the transesterification reaction. The S,S,S-[2,2,2-(1,2,4-cyclohexanetriyl)triethyl] tristhioacetate intermediate (3,090 grams, 7.9 mol.) was charged to a 5-liter round bottom flask. Ethanol (1,070 grams, 23.3 mol.) and sodium ethoxide (68.6 grams) were added with stirring. The mixture was heated to refluxing conditions for 4 hours and the ethyl acetate that formed was removed by distillation at atmospheric pressure. An additional amount of ethanol (672 grams, 15.6 mol.) was added and the mixture was refluxed overnight. The ethanol and ethyl acetate were removed by distillation. The addition of ethanol and removal of ethanol and ethyl acetate were repeated two more times. The 1,2,4-tris(2-mercaptoethyl)cyclohexane intermediate (1,884 grams) was a pale yellow hazy liquid.

The chlorination of the mercaptan was done using chlorine gas. 1,2,4-Tris(2-mercaptoethyl)cyclohexane (124 grams, 0.47 mol.) and carbon tetrachloride (2,964 grams) were charged into a 5-liter round bottom flask. The solution was cooled using an ice bath and purged with nitrogen gas. Chlorine gas (100 grams, 1.41 mol.) was bubbled into the solution using a fritted tube for 2.9 hours.

A slurry of dried sodium toluene sulfinate (254 grams, 1.42 mol) and carbon tetrachloride (939 grams) was added to the chlorinated sulfur-containing intermediate, 1,2,4-tris-(3-chloro-3-thia-propyl)cyclohexane, prepared above over a 30 minutes. The temperature was maintained with an ice bath below 26° C. Tetrahydrofuran (271 grams) was added and the mixture was stirred overnight at room temperature. The solution was filtered and the carbon tetrachloride and tetrahydrofuran were removed under reduced pressure. Toluene-4-thiosulfonic acid S-{2-[bis-2,4-(2-toluene-4-sulfonylsulfanyl-ethyl)-cyclohexyl]-ethyl}ester, a low melting solid, was produced in quantitative yield.

EXAMPLE 2

This example illustrates the preparation of toluene-4-thiosulfonic acid S-{2-[bis-2,4-(2-toluene-4-sulfonylsulfanyl-ethyl)-cyclohexyl]-ethyl}ester.

A solution of 1,2,4-tris-(2-mercaptoethyl)cyclohexane (130 grams, 0.48 mol.) in carbon tetrachloride (100 milliliter) was slowly added over a period of 1.6 hours to a slurry of N-chlorosuccinimide (213 grams, 1.59 mol.) in carbon tetrachloride (1 liter) in a 3-liter and 3-neck round bottom flask equipped with a condenser, mechanical stirrer and a nitrogen gas inlet. The mixture was maintained at a temperature of less than 27° C. The 1,2,4-tris-(2-mercaptoethyl)cyclohexane was prepared by the procedure in Example 1. After addition, the mixture was stirred at ambient temperature for 2.5 hours then filtered to remove succinimide. The succinimide solid was washed with carbon tetrachloride (150 milliliters) and the filtrate added to the reaction mixture. The reaction mixture was added slowly over a period of 1.5 hours to a slurry of sodium toluene sulfinate (300 grams, 1.7 mol.) in tetrahydrofuran (700 milliliters) while maintaining the temperature less than 25° C. The mixture was stirred for 2.5 hours, filtered through Celite and the filtrate was stripped under vacuum by slowly increasing vacuum from 100 mm Hg to less than 1 mm Hg while maintaining the temperature in a range of 60 to 70° C. A viscous orange oil (326 grams, 93% yield) was obtained. $^1$H NMR(CDCl$_3$) δ: 7.80 (d, J=7.6 Hz, 6 H); 7.36 (d, J=7.6 Hz, 6H); 2.8-3.1 (m, 6H); 2.45 (s, 9H); 0.4-1.9 (m, 15H).

EXAMPLE 3

This example illustrates the preparation of an isomeric mixture containing 84.82 weight percent cis-toluene-4-thiosulfonic acid S-{2-[cis,cis-bis-2,4-(2-toluene-4-sulfonylsulfanyl-ethyl)-cyclohexyl]-ethyl}ester.

A mixture of stereochemical isomers of 1,2,4-trivinylcyclohexane was prepared by fractional distillation. The distillation unit consisted of a 5-liter round bottom flask, a strip silvered column (inner diameter of 51 mm, height of 1,470 mm) equipped with stainless steel flat mesh screen supporting a 316 stainless steel Propac 0.16 mesh ball, size rating 0.16 inch packing material, and a reflux condenser. Trivinylcyclohexane (4,150 grams) and 4-tert-butylcatechol (4.5 grams) were charged to the flask. The pressure was reduced to within the range of 6.5 torr to 7.3 torr and the temperature to within the range of 90.0° C. to 90.8° C. The boiling rate was maintained at 6 drops per second. The distillate was collected and analyzed by gas chromatography. The gas chromatography column and conditions were a DB-5 column, 30 meters long, 0.32 millimeter internal diameter, 0.25 micron film, a flame ionization detector, 60 psi air, 50 psi helium and 30 psi hydrogen pressure. The temperature profile had a starting temperature of 80° C., a ramp at 10° C. per minute to 25° C., a hold for 10 minutes at 250° C., a second ramp at 10° C. per minute to 300° C. and a final hold of 5 minutes at 300° C. The mixture was composed of a low boiling isomer (84.2 weight percent), a slightly higher boiling isomer (14.4 weight percent) and a mixture of two high boiling isomers (1.3 weight percent). The low boiling component was assigned to the cis,cis,cis-1,2,4-trivinylcyclohexane. The other three isomers contain both cis and trans stereochemistry.

The 1,2,4-trivinylcyclohexane containing 84.2 weight percent cis,cis,cis-1,2,4-trivinylcyclohexane isomer, was used to prepare an isomeric mixture containing 84.2 weight percent cis-toluene-4-thiosulfonic acid S-{2-[cis,cis-bis-2,4-(2-toluene-4-sulfonylsulfanyl-ethyl)-cyclohexyl]-ethyl}ester according to the procedures of Example 1.

COMPARATIVE EXAMPLE 1

This example illustrates the preparation of the compound 1-toluene-4-thiosulfonic acid S-(6-toluene-4-sulfonylsulfanyl)hexyl ester whose structure is:

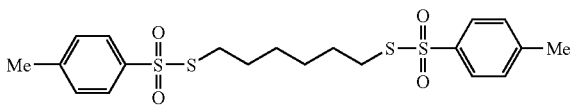

1,6-Dibromohexane (39.6 gram, 0.325 mol.), sodium thiotosylate (77.9 grams, 0.325 mol., based on purity) and acetone (225 milliliters) were charged into a round bottom flask equipped with a condenser and heated to reflux under nitrogen overnight. The solution was cooled and the solvent was stripped off on a rotary evaporator. The solid residue was then partitioned between chloroform and water. The bottom organic layer was then washed with water and saturated sodium chloride solution. After drying over anhydrous sodium sulfate, the chloroform was stripped under vacuum yielding approximately 82 g of crude product. This material was then recrystallized from 210 milliliter ethanol and dried overnight in a vacuum oven at 50° C. The final yield was 71.0 grams or 95% yield with a melting point of 86-88° C. Proton NMR (CDCl$_3$) δ: 1.27 (m, 4H), 1.57 (m, 4H), 2.48 (s, 6H, CH$_3$—Ar), 2.96 (t, J=6 Hz, 4H, CH$_2$—S), 7.37 (d, J=8 Hz, 4H, Ar—H), 7.82 (d, J=8 Hz, 4H, Ar'—H).

COMPARATIVE EXAMPLE 2

This example illustrates the preparation of the compound trimethylolpropane tris(3-p-toluenethiosulfonato propionate) whose structure is:

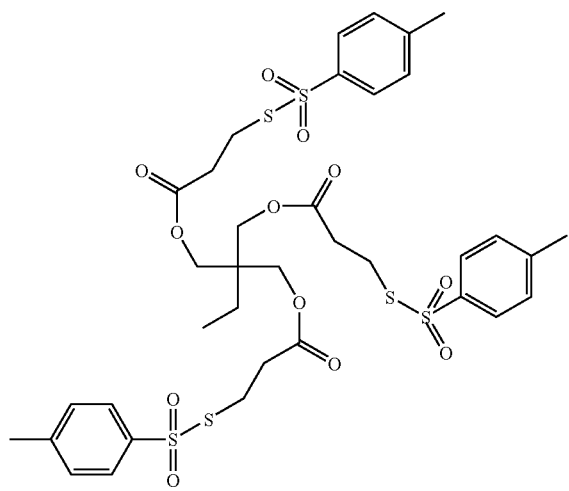

N-chlorosuccinimide (13.3 grams, 0.099 mol) was slurried with carbon tetrachloride (100 milliters) in a 500-milliliter, 3-neck flask equipped with a thermocouple, mechanical stirrer and dropping funnel, and nitrogen gas atmosphere. A solution of trimetholpropane tris-(3-mercapto propionate) (12.0 grams, 0.030 mol) in carbon tetrachloride (20 milliliters) was added over 11 minutes while maintaining the temperature below 25° C. The reaction medium was stirred at ambient temperature for 4 hours after which it was filtered. The filtrate was added over 45 minutes to a slurry of sodium toluenesulfinate (17.7 grams, 0.099 mol.) in tetrahydrofuran (50 milliliters). After 15 hours of reaction, the mixture was filtered through Celite to provide a clear yellow solution. The solution was concentrated and devolatilized to yield 18.0 grams of a thick, light yellow oil. $^1$H NMR(CDCl$_3$) δ: 7.81 (d, J=7.9 Hz, 6H); 7.36 (d, J=7.9 Hz, 6H); 3.98 (s, 6H); 3.16 (t, J=6.6 Hz, 6H); 2.75 (t, J=6.6 Hz, 6H); 2.45 (s, 9H); 1.41 (q, J=7.5 Hz, 2H); 0.85 (t, J=7.5 Hz, 3H). $^{13}$C{$^1$H} NMR (CDCl$_3$): 170.7, 145.2, 141.4, 130.0, 127.1, 68.0, 40.7, 4.0, 29.6, 22.8, 21.7, 7.3 ppm.

COMPARATIVE EXAMPLE 3

This example illustrates the preparation of the compound pentaerythritol tetrakis(3-p-toluenethiosulfonato propionate) whose structure is:

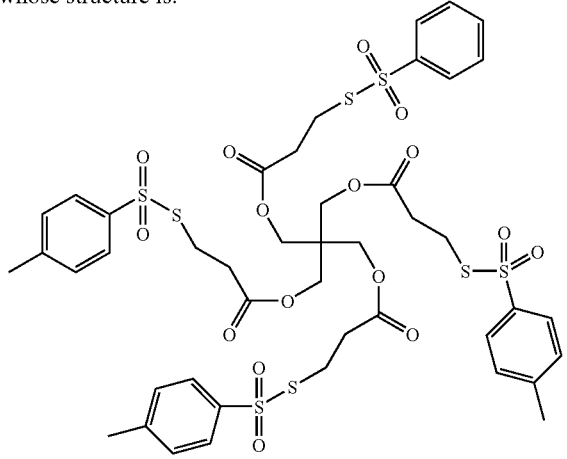

N-chlorosuccinimide (18.0 grams, 0.135 mol.) was slurried with carbon tetrachloride (130 milliliters) in a 500-milliliter, 3-neck flask equipped with a thermocouple, mechanical stirrer and dropping funnel, and nitrogen gas atmosphere. A solution of pentaerythritol tetrakis(3-mercapto propionate) (15.0 grams, 0.0307 mol.) in carbon tetrachloride (30 milliliters) and chloroform (30 milliliters) was added over 45 minutes while maintaining the temperature under 26° C. The solid material which formed was filtered and washed with carbon tetrachloride (50 milliliters) and the washing combined with the filtrate. The filtrate was added over a 30-minute period to a slurry of sodium toluenesulfinate (24 grams, 0.135 mol.) in tetrahydrofuran (80 milliters). After 2 hours, the reaction mixture was filtered through Celite to provide a clear yellow solution. The filtrate was concentrated and devolatilized to provide 12.0 grams of a thick, light brown oil. $^1$H NMR(CDCl$_3$) δ: 7.82 (d, J=7.9 Hz, 8H); 7.37 (d, J=7.9 Hz, 8H); 4.08 (s, 8H); 3.16 (t, J=6.6 Hz, 8H); 2.78 (t, J=6.6 Hz, 8H); 2.45 (s, 12H). $^{13}$C{$^1$H} NMR(CDCl$_3$): 170.5, 145.2, 141.4, 130.1, 127.1, 68.0, 44.3, 33.9, 30.4, 25.6 ppm.

EXAMPLE 4

This example illustrates the preparation of the compound 1,2,4-tris(2-sodium thiosulfonatoethyl)cyclohexane whose structure is:

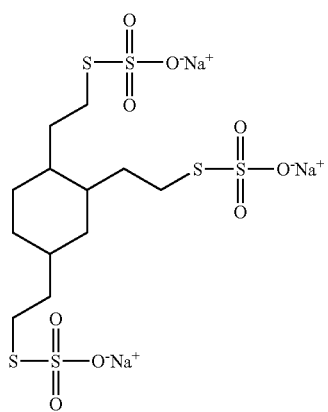

Anhydrous hydrogen bromide gas was bubbled through a solution of 1,2,4-trivinylcyclohexane (10.0 grams, 0.072 mol.) in pentane (100 milliliters) for a period of 7hours. Nitrogen gas was bubbled through the flask for 30 minutes after which the solution was washed with saturated sodium bicarbonate (200 milliliters) and water until the pH of the filtrate was neutral. The organic phase was dried over magesium sulfate, filtered and stripped under vacuum to yield 22.5 grams of a slightly yellowish brown oil that darkened on standing. $^1$H NMR(CDCl$_3$) δ: 3.3-3.6 (m, 6H); 0.6-2.2 (s, 15H).

Crude 1,2,4-tris-(2-bromoethyl)cyclohexane (1.5 gram, 0.037 mol.) was dissolved in tetrahydrofuran (20 milliliters) and sodium thiosulfate pentahydrate (3.03 grams, 0.0122 mol.) in water (20 milliliters). A two-phase system formed into which acetone (10 milliliters) and ethanol (5 milliliters) were added. The reaction mixture was heated at 65° C. for 15 hours. The volatiles were removed under reduced pressure and a viscous yellow product was obtained. $^1$H NMR(CDCl$_3$) δ: 2.8-3.2 (m, 6H); 0.6-2.0 (s, 15H).

COMPARATIVE EXAMPLES 4-6; EXAMPLES 5 AND 6

A model low rolling resistance passenger tire tread formulation as described in Table 1 below and a mix procedure were used to evaluate representative examples of the sulfur-containing cycloaliphatic compounds of the present invention. The mixing was done as follows in a "B" BANBURY® (Farrell Corp.) mixer with a 103-cubic inch (1,690-centimeter) chamber volume. The mixing of the rubber was done in two steps. The mixer was turned on with the mixer at 80 rpm and the cooling water at 71° C. The rubber polymers were added to the mixer and ram down mixed for 30 seconds. The silica and the other ingredients in the masterbatch of Table 1 except for the silane coupling agent, curatives and the oils were added to the mixer and ram down mixed for 60 seconds. The mixer speed was reduced to 35 rpm after which the silane and oils of the materbatch were added to the mixer and ram down mixed for 60 seconds. The mixer throat was dusted down and the ingredients ram down mixed until the temperature reached 149° C. The ingredients were then mixed for an additional 3 minutes and 30 seconds. The mixer speed was adjusted to maintain the temperature between 152° C. and 157° C. The rubber was dumped (removed from the mixer), a sheet was formed on a roll mill set at about 85° C. to 88° C., and then allowed to cool to ambient temperature.

In the second step, the masterbatch was recharged into the mixer. The mixer's speed was 80 rpm, the cooling water was set at 71° C. and the batch pressure was set at 6 MPa. The masterbatch was ram down mixed for 30 seconds, the temperature of the masterbatch was then brought up to 149° C. after which the mixer's speed was reduced to 32 rpm and the rubber mixed for 3 minutes and 20 seconds at a temperature between 152° C. and 157° C. After mixing, the rubber was dumped from the mixer, the sulfur-containing cycloaliphatic compound and curative were added and mixed and a sheet was formed on a roll mill set at about 85° C. to 88° C., and then allowed to cool to ambient temperature.

Measurements and Testing of the Rubber Compositions

The measurements made and the tests used to characterize the rubber compositions are described below. The rubber compositions were characterized before and after curing as indicated below.

The Theological properties of the compositions were measured on a Monsanto R-100 Oscillating Disk Rheometer and a Monsanto M1400 Mooney Viscometer. The specimens for measuring the mechanical properties were cut from 6 mm plaques cured for (t90+1) minutes at 149° C. Curing and testing of the cured rubber compositions in the form of plaques were carried out according to ASTM standards. In addition, small strain dynamic tests were carried out on a Rheometrics Dynamic Analyzer (ARES-Rheometrics Inc.). Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$ and $\tan \delta_{max}$, were extracted from the non-linear responses of the rubber compounds at small strains. In some cases, steady state values of tan δ were measured after 15 minutes of dynamic oscillations at strain amplitudes of 35% (at 60° C.). Temperature dependence of dynamic properties was also measured from about −80° C. to +80° C. at small strain amplitudes (1 or 2%) at a frequency of 10 Hz.

The specific curing procedure and measurement procedures were as follows:

| Curing Procedure/Measurement | Testing Standard |
| --- | --- |
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

The results are presented in Table 2.

TABLE 1

Summer Passenger Car Tread Compounding Formulations

| Masterbatch | Comp. Ex. 4 phr | Ex. 5 phr | Ex. 6 phr | Ex. 7 phr | Ex. 8 phr |
| --- | --- | --- | --- | --- | --- |
| Styrene-butadiene rubber | 77 | 77 | 77 | 77 | 77 |
| Cis Butyl rubber | 23 | 23 | 23 | 23 | 23 |
| Silica | 95 | 95 | 95 | 95 | 95 |
| Carbon black | 3.0 | 3.0 | 3.0 | 3.0 | 3.0 |
| Aromatic oil | 35.0 | 35.0 | 35.0 | 35.0 | 35.0 |
| Stearic Acid | 2.5 | 2.5 | 2.5 | 2.5 | 2.5 |
| Zinc Oxide | 2.5 | 2.5 | 2.5 | 2.5 | 2.5 |
| 6PPD | 2.0 | 2.0 | 2.0 | 2.0 | 2.0 |
| TMQ | 2.0 | 2.0 | 2.0 | 2.0 | 2.0 |
| Wax | 2.0 | 2.0 | 2.0 | 2.0 | 2.0 |
| Silane | 8.075 | 8.075 | 8.075 | 8.075 | 8.075 |
| Masterbatch | 252.1 | 252.1 | 252.1 | 252.1 | 252.1 |
| Sulfur | 2.0 | 2.0 | 2.0 | 2.0 | 2.0 |
| CBS | 2.0 | 2.0 | 2.0 | 2.0 | 2.0 |
| DPG | 2.0 | 2.0 | 2.0 | 2.0 | 2.0 |
| Compound from Ex. 1 | | 1.675 | | 3.35 | |
| Compound from Ex. 4 | | | 1.325 | | 2.65 |

The commercial sources of the components of the tread formulations of Table 1 are as follows: styrene-butadiene rubber: Buna VSL 5025 (non-oil extended) from Lanxess; silica: Zeosil 1165MP from Rhodia; carbon black (N-330); process oil: Sundex 8125 from Sun Oil; ZnO: Kadox 720C from ZincCorp.; stearic acid: Industrene R from Witco, Crompton; 6 PPD:(Flexzone 7P from Uniroyal); TMQ: Naugard Q from Crompton; wax: Sunproof Improved from Uniroyal, Crompton; sulfur: Rubbermakers Sulfur 104 from Harwick; CBS: Delac S from Uniroyal, Crompton; DPG: DPG from Uniroyal, Crompton; silane: Silquest A-1589 silane from Momentive Performance Materials.

TABLE 2

Summer Passenger Car Tread Compounding Results

| Rubber Composition, Properties | Units | Comp. Ex. 4 | Ex. 5 | Ex. 6 | Ex. 7 | Ex. 8 |
| --- | --- | --- | --- | --- | --- | --- |
| Cure, t95 | Min. | 14.57 | 17.47 | 11.87 | 20.03 | 13.82 |
| $M_H$-$M_L$ | | 27.82 | 28.81 | 23.71 | 33.78 | 23.25 |
| 50% Modulus | MPa | 1.3 | 1.3 | 1.0 | 1.6 | 1.0 |
| 100% Modulus | MPa | 2.4 | 2.9 | 1.9 | 3.9 | 1.8 |
| 300% Modulus | MPa | 15.2 | — | 15.0 | — | 11.7 |
| Tensile | MPa | 17.1 | 16.2 | 15.4 | 15.1 | 14.4 |
| Elongation | % | 332 | 264 | 311 | 220 | 326 |
| Hardness RT | Shore A | 61.0 | 58.9 | 52.5 | 62.9 | 53.2 |
| Rebound RT | % | 38.6 | 41.8 | 41.7 | 40.0 | 40.9 |
| Rebound 70° C. | % | 60.1 | 63.7 | 62.4 | 66.7 | 60.1 |
| Delta rebound | | 21.5 | 21.9 | 20.7 | 26.7 | 19.2 |
| Tear Strength | N | 34.6 | 38.4 | 32.4 | 36.7 | 32.2 |

These experimental tests demonstrate the improved performance of the rubber compositions formulated with sulfur-containing cycloaliphatic compounds of the present invention compared with the same rubber compositions lacking these additives. For example, the tear strength and delta rebound of the compound containing 3.35 phr toluene-4-thiosulfonic acid S-{2-[bis-2,4-(2-toluene-4-sulfonylsulfanyl-ethyl)-cyclohexyl]-ethyl}ester (Example 5) showed a 7 percent and 24 percent improvement, respectively, over a rubber composition not containing this additive (Comparative Example 5) and a similar 14 percent and 40 percent improvement, respectively, over a rubber composition containing 1,2,4-tris(2-sodium thiosulfonatoethyl)cyclohexane additive (Comparative Example 7).

COMPARATIVE EXAMPLE 5; EXAMPLES 9-11

The effect of the amount of the sulfur-containing cycloaliphatic additive on the performance of the rubber compositions was evaluated. The rubber compounds were prepared, cured and tested according the procedures in Example 5. The rubber formulations were identical to those in Comparative Example 4 and Example 5, except for the amounts of toluene-4-thiosulfonic acid S-{2-[bis-2,4-(2-toluene-4-sulfonylsulfanyl-ethyl)-cyclohexyl]-ethyl}ester added, which are presented in Table 3.

The results indicate an increase in 300% modulus and tensile as the amounts of toluene-4-thiosulfonic acid S-{2-[bis-2,4-(2-toluene-4-sulfonylsulfanyl-ethyl)-cyclohexyl]-ethyl}ester were increased.

TABLE 3

Summer Passenger Car Tread Compounding Formulation and Results

| | Units | Comp. Ex. 5 | Ex. 9 | Ex. 10 | Ex. 11 |
| --- | --- | --- | --- | --- | --- |
| Amount of Additive from Ex. 1 | phr | 0 | 1.78 | 3.56 | 5.33 |
| Property | Units | | | | |
| Specific Gravity | g/cm³ | 1.209 | 1.209 | 1.212 | 1.212 |
| 50% Modulus | MPa | 1.26 | 1.39 | 1.87 | 2.15 |
| 100% Modulus | MPa | 2.06 | 2.23 | 3.12 | 3.64 |
| 300% Modulus | MPa | 8.96 | 9.10 | 12.75 | 14.25 |
| Tensile | MPa | 13.95 | 14.63 | 14.61 | 14.91 |
| Elongation | % | 449 | 458 | 363 | 340 |
| Shore A RT | Shore A | 70.7 | 70.7 | 78.1 | 80.3 |
| Shore A 70° C. | Shore A | 67.5 | 66.5 | 74.4 | 76.0 |
| Rebound RT | % | 24.2 | 25.2 | 25.1 | 25.1 |
| Rebound 70° C. | % | 42.6 | 41.2 | 42.1 | 41.9 |

TABLE 3-continued

Summer Passenger Car Tread Compounding Formulation and Results

|  | Units | Comp. Ex. 5 | Ex. 9 | Ex. 10 | Ex. 11 |
|---|---|---|---|---|---|
| Graves Tear (100 C.) |  | 36.3 | 55.4 | 50.0 | 46.0 |
| Fatigue to failure |  | 23.55 | 23.25 | 5.8 | 3.75 |
| E' mean | MPa | 8.1 | 9.7 | 10.1 | 11.7 |

COMPARATIVE EXAMPLE 6-10; EXAMPLES 12 AND 13

Rubber compositions were prepared wherein the formulations were based on natural rubber (NR). These formulations are representative for rubber compositions used in truck tire tread. The mixing, curing and testing procedures were identical to Comparative Example 8. The formulation is presented in Table 4. The results are presented in Table 5.

TABLE 4

Truck NR Tread Compounding Formulations

| Masterbatch | Comp. Ex. 6 phr | Ex. 12 phr | Ex. 13 phr | Comp. Ex. 7 phr | Comp. Ex. 8 phr | Comp. Ex. 9 phr | Comp. Ex. 10 phr |
|---|---|---|---|---|---|---|---|
| Natural Rubber | 100 | 100 | 100 | 100 | 100 | 100 | 100 |
| Carbon black | 48.5 | 48.5 | 48.5 | 48.5 | 48.5 | 48.5 | 48.5 |
| Mineral oil | 2.4 | 2.4 | 2.4 | 2.4 | 2.4 | 2.4 | 2.4 |
| Stearic Acid | 2.0 | 2.0 | 2.0 | 2.0 | 2.0 | 2.0 | 2.0 |
| Zinc Oxide | 3.0 | 3.0 | 3.0 | 3.0 | 3.0 | 3.0 | 3.0 |
| 6PPD | 1.5 | 1.5 | 1.5 | 1.5 | 1.5 | 1.5 | 1.5 |
| DTPD | 1.0 | 1.0 | 1.0 | 1.0 | 1.0 | 1.0 | 1.0 |
| Wax | 2.5 | 2.5 | 2.5 | 2.5 | 2.5 | 2.5 | 2.5 |
| Masterbatch | 160.9 | 160.9 | 160.9 | 160.9 | 160.9 | 160.9 | 160.9 |
| Sulfur | 1.4 | 1.4 | 1.4 | 1.4 | 1.4 | 1.4 | 1.4 |
| TBBS | 1.6 | 1.6 | 1.6 | 1.6 | 1.6 | 1.6 | 1.6 |
| CTP | 0.1 | 0.1 | 0.1 | 0.1 | 0.1 | 0.1 | 0.1 |
| Additive from Ex. 1 |  | 1.69 | 3.37 |  |  |  |  |
| Additive from Comp. Ex. 3 |  |  |  | 2.99 | 5.99 |  |  |
| Additive from Comp. Ex. 2 |  |  |  |  |  | 3.84 | 4.61 |

The commercial sources of the tread formulations of Table 4 are as follows: natural rubber: (SMR-L); TBBS: Delac NS from Uniroyal; CTP: carbon treated phthalic anhydride retarder from Lanxess; carbon black (N-330); zinc oxide: Kadox 720C from ZincCorp.; stearic acid: Industrene R from Witco, Crompton; 6PPD: Flexzone 7P from Uniroyal; wax: Sunproof Improved from Uniroyal, Crompton; sulfur: Rubbermakers Sulfur 104 from Harwick.

TABLE 5

Truck Natural Rubber Tread Compounding Results

| Rubber Composition, Property | Units | Comp. Ex. 6 | Ex. 12 | Ex. 13 | Comp. Ex. 7 | Comp. Ex. 8 | Comp. Ex. 9 | Comp. Ex. 10 |
|---|---|---|---|---|---|---|---|---|
| Cure, t95 | Min. | 11.4 | 14.07 | 16.84 | 14.22 | 17.53 | 14.72 | 14.42 |
| $M_H$-$M_L$ |  | 35.48 | 39.57 | 39.56 | 39.31 | 38.76 | 39.13 | 41.61 |
| 50% Modulus | MPa | 1.3 | 1.6 | 1.8 | 1.7 | 1.8 | 1.9 | 2.1 |
| 100% Modulus | MPa | 2.66 | 2.91 | 3.24 | 3.10 | 3.29 | 3.15 | 3.39 |
| 300% Modulus | MPa | 14.63 | 14.51 | 14.68 | 14.42 | 14.47 | 13.68 | 14.22 |
| Tensile | MPa | 31.13 | 29.91 | 30.29 | 29.76 | 25.88 | 27.69 | 28.67 |
| Elongation | % | 524 | 511 | 521 | 528 | 466 | 512 | 514 |
| Hardness RT | Shore A | 63.0 | 68.1 | 70.6 | 69.5 | 71.5 | 72.8 | 74.3 |
| Rebound RT | % | 52.9 | 53.1 | 46.6 | 43.3 | 50.5 | 52.8 | 50.6 |
| Rebound 70° C. | % | 63.1 | 66.2 | 57.7 | 54.6 | 63.5 | 65.4 | 63.4 |
| Delta rebound |  | 13.1 | 11.3 | 9.8 | 11.1 | 11.3 | 7.9 | 7.3 |
| Tear Strength | N | 280.4 | 263.7 | 264.0 | 262.5 | 247.1 | 268.0 | 252.0 |

COMPARATIVE EXAMPLES 11 AND 12, EXAMPLE 14

The rubber compositions of these examples were prepared, cured and tested in accordance with the procedures of Comparative Example 5. The formulations for the natural rubber formulations are given in Table 6, below. The examples explore the effects of adding toluene-4-thiosulfonic acid S-{2-[bis-2,4-(2-toluene-4-sulfonylsulfanyl-ethyl)-cyclohexyl]-ethyl}ester as compared to adding 1-toluene-4-thiosulfonic acid S-(6-toluene-4-sulfonylsulfanyl) hexyl ester to the natural rubber compositions. The test results are presented in Table 7, below.

TABLE 6

Truck Natural Rubber Tread Compounding Formulations

| Masterbatch | Comp. Ex. 11 phr | Comp. Ex. 12 phr | Ex. 14 phr |
|---|---|---|---|
| Natural rubber | 100 | 100 | 100 |
| Carbon black | 43.5 | 43.5 | 43.5 |
| DPTD | 1 | 1 | 1 |
| Wax | 2.5 | 2.5 | 2.5 |
| Zinc oxide | 3 | 3 | 3 |
| Stearic acid | 2 | 2 | 2 |
| 6-PPD | 1.5 | 1.5 | 1.5 |
| TMQ | 1 | 1 | 1 |
| TBBS | 1.1 | 1.1 | 1.1 |
| Sulfur | 1.8 | 1.6 | 1.1 |
| Additive from Ex. 1 | | | 2.25 |
| Additive from Comp. Ex. 1 | | 0.95 | |

The commercial souces of the components employed in the tread formulations of Table 6 are as follows: natural rubber: (SMR-L); TBBS: Delac NS from Uniroyal; TMQ: Naugard Q from Crompton; carbon black (N-330); zinc oxide: Kadox 720C from ZincCorp.; stearic acid: Industrene R from Witco, Crompton; 6PPD: Flexzone 7P from Uniroyal; wax: Sunproof Improved from Uniroyal, Crompton; sulfur: Rubbermakers Sulfur 104 from Harwick.

The test results are presented in Table 7.

TABLE 7

Truck Natural Rubber Tread Compounding Results

| Rubber Composition, Property | Units | Comp. Ex. 11 | Comp. Ex. 12 | Ex. 14 |
|---|---|---|---|---|
| Density RT | g/cm$^3$ | 1.09 | 1.09 | 1.09 |
| Hardness RT | Shore A | 56.9 | 59.5 | 60.9 |
| Hardness 70 C. | Shore A | 51.6 | 55.3 | 54.6 |
| Tensile Strength | MPa | 20.9 | 23.3 | 21.7 |
| Elongation | % | 559 | 562 | 571 |
| 100% Modulus | MPa | 1.57 | 1.86 | 1.72 |
| 300% Modulus | MPa | 8.87 | 10.16 | 9.02 |
| Break Energy Density | J/cm$^3$ | 42.2 | 48.5 | 45.3 |
| HSTE | MJ/cm$^3$ | 10.13 | 9.18 | 13.03 |
| Graves Tear | | 60.02 | 60.52 | 73.2 |

The rubber compositions containing the sulfur-containing cycloaliphatic compound of the present invention, toluene-4-thiosulfonic acid S-{2-[bis-2,4-(2-toluene-4-sulfonylsulfanyl-ethyl)-cyclohexyl]-ethyl}ester, shows a 22 percent and 21 percent improvement in Graves Tear, as measured by ASTM D1004 Standard Test Method for Tear Resistance (Graves Tear), when compared to rubber compositions containing no additive and a difunctional additive, 1-toluene-4-thiosulfonic acid S-(6-toluene-4-sulfonylsulfanyl)hexyl ester, while maintaining the other physical properties.

COMPARATIVE EXAMPLES 13 AND 14 AND EXAMPLE 15

The compounds in Table 8 were mixed in an instrumented "OOC" BANBURY® mixer with a 2,600 cubic centimeter chamber volume. The mixing of the rubber was done in three steps. The mixer was turned on with the mixer at 80 rpm and the cooling water at 71° C. The rubber polymers were added to the mixer and were ram down mixed for 30 seconds. The fillers and the silane were added to the mixer and were ram down mixed for 30 seconds. The other ingredients of the rubber compound of Table 8 except for the oils were added to the mixer and were down ram down mixed for 60 seconds. The mixer speed was reduced to 65 rpm and then the oils were added to the mixer and were ram down mixed for 60 seconds. The mixer throat was dusted down and the ingredients were ram down mixed until the temperature reached 150° C. The ingredients were then mixed for an additional 3 minutes and 30 seconds. The mixer speed was adjusted to hold the temperature between 150° C. and 155° C. The rubber was dumped (removed from the mixer), a sheet was formed on a roll mill set at about 85° C. to 90° C., and then was allowed to cool to ambient temperature.

In the second step, the rubber compound prepared in the first step was recharged into the mixer. The mixer's speed was 80 rpm, the cooling water was set at 71° C. and the ram pressure was set at 25 psi. The rubber compound prepared in the first step was ram down mixed for 150 seconds while the temperature of the mixture was brought up to 150° C., and then the mixer was reduced to 50 rpm. The rubber was mixed for 40 seconds at temperatures between 150° C. and 155° C. After mixing, the rubber was dumped (removed from the mixer) and a sheet was formed on a roll mill set at about 85° C. to 90° C. The rubber was allowed to cool to ambient temperature.

In a third step, the mixer speed was set to 50 rpm, the cooling water was set at 71° C. and the ram pressure was set at 25 psi. The rubber compound prepared in the second step and the curatives were ram down mixed for 190 seconds while the temperature of the final mixture was brought up to 115° C. After mixing, the rubber was dumped (removed from the mixer), a sheet was formed on a roll mill set at about 85° C. to 90° C., and then was allowed to cool to ambient temperature. The curing condition was 160° C. for 20 minutes.

The performance of the sulfur-containing cycloaliphatic compounds of the present invention is demonstrated in a truck tread composition. The formulation is given in Table 8 and the results in Table 9. The test procedures were described in the following ASTM and DIN methods:

| Mooney Scorch | ASTM D1646 |
|---|---|
| Mooney Viscosity | ASTM D1646 |
| Rheometer (MDR 2000) | DIN 53 529 |
| Storage Modulus, Loss Modulus, Tensile and Elongation | DIN 53 504-R1 |
| Shore A Hardness | DIN 53 505 |
| Rebound | DIN 53 512, ASTM D1054 |
| DIN Abrasion | DIN 53 516 |

TABLE 8

Truck Tread Compounding Formulation

| Ingredients | Comp. Ex. 13 phr | Comp. Ex. 14 phr | Ex. 15 phr |
|---|---|---|---|
| Natural rubber | 100 | 100 | 100 |
| Carbon black N-220 | 43.5 | 43.5 | 43.5 |
| Stearic Acid | 2.0 | 2.0 | 2.0 |
| Zinc Oxide | 3.0 | 3.0 | 3.0 |
| Anti-aging | 6.0 | 6.0 | 6.0 |
| Sulfur | 1.8 | 1.8 | 1.8 |
| TBBS | 1.1 | 1.1 | 1.1 |
| DBTCH | | 0.95 | |
| Crosslinker from Example 1 | | | 2.78 |

The commercial sources of the components of the tread formulations of Table 8 are as follows: natural rubber: (SMR-L); carbon black (N-220); ZnO: Kadox 720C from ZincCorp.; stearic acid: Industrene R from Witco, Crompton; TBBS: Delac NS from Uniroyal, Crompton; DBTCH: Vulcuren from Lanxess; sulfur: Rubbermakers Sulfur 104 from Harwick.

TABLE 9

Truck Tread Results

| Rubber Composition, Property | Units | Comp. Ex. 13 | Comp. Ex. 14 | Ex. 15 |
|---|---|---|---|---|
| Specific Gravity | g/cm$^3$ | 1.09 | 1.09 | 1.09 |
| Mooney (ML1 + 4) at 100° C. | Mooney units | 60 | 59.3 | 60.3 |
| MDR 2000 at 160° C. | | | | |
| Time (Cure state) - 10 | Min. | 2.41 | 2.20 | 2.28 |
| Time (Cure state) - 95 | Min. | 5.92 | 6.05 | 7.6 |
| ML | dNm | 2.52 | 2.53 | 2.67 |
| MHF | dNm | 15.15 | 16.10 | 15.12 |
| MHF-ML | dNm | 12.63 | 13.57 | 12.45 |
| 50% Modulus | MPa | 0.96 | 1.10 | 1.07 |
| 300% Modulus | MPa | 8.87 | 10.16 | 9.02 |
| Tensile | MPa | 20.9 | 23.3 | 21.7 |
| Elongation | % | 559 | 562 | 517 |
| Shore A RT | Shore A | 56.9 | 59.5 | 60.9 |
| Resilience RT | % | 45.7 | 46.8 | 43.6 |
| Rebound 70 C. | % | 56.9 | 57.9 | 52.4 |
| Break energy density | J/cm$^3$ | 42.2 | 48.5 | 45.3 |
| Graves 100° C. tear resistance | N/mm | 60.02 | 60.52 | 73.20 |
| Epl. temperature sweep 50/30 N | | | | |
| Tg (E") | ° C. | −61.3 | −61.2 | 61.2 |

The truck tread showed 22 percent and 21 percent increase in Graves tear resistance when compared to the compounds containing not sulfur-containing cycloaliphatic compounds and DBTCH, respectfully. The Graves tear resistance is an indicator of improved wear under harsh conditions.

Although the rubber compositions referred to in the examples above have been described as truck tread compositions, these rubber compositions are expected to be suitable for other industrial rubber-based goods, including, illustratively, for conveyor belts.

EXAMPLE 16

A model shoe sole formulation as described in Table 10 below and a mix procedure are used to evaluate representative examples of the thiocarbamoyldisulfanyl-functional cycloaliphatic compounds of the present invention. The mixing is done as follows in a "B" BANBURY® (Farrell Corp.) mixer with a 103-cubic inch (1,690-cubic centimeter) chamber volume. The mixing of the rubber is done in two steps. The first step is to prepare a rubber compound without curatives. The mixer is turned on with the mixer at speed number 2 and full cooling water. The rubber polymers are added to the mixer and are ram down mixed for 30 seconds. Half of the silica is added to the mixer and are ram down mixed for 30 seconds. Half of the silica and the oil are added to the mixer and are ram down mixed for 30 seconds. All of the remaining ingredients of the rubber compound except for the curatives are added to the mixer and are ram down mixed for 30 seconds. The mixer is dust down and is ram down mixed for 15 seconds, and then the mixer speed is increased to number 3 and mixture is ram down mixed for an additional 15 seconds. The rubber is dumped (removed from the mixer), a sheet is formed on a roll mill set at about 49° C. to 55° C., and then is allowed to cool to ambient temperature.

In the second step, the final mixture is prepared. The rubber compound prepared in the first step is recharged into the roll mill at about 49° C. to 55° C. and the curative package is added. The curative package is mixed in and then is cut six times on each side. A sheet is formed on a roll mill set and then is allowed to cool to ambient temperature.

TABLE 10

Model Shoe Sole Compounding Formulation Example 16

| Ingredients | Phr |
|---|---|
| Natural rubber | 20 |
| Nitrile rubber | 20 |
| Cis-Butyl rubber | 60 |
| Silica | 42 |
| Diethylene glycol | 2 |
| BHT | 1 |
| Zinc Oxide | 4.0 |
| Stearic acid | 1 |
| Activator | 1.5 |
| Disperser | 2.0 |
| Homogenizer | 2 |
| Wax | 1.0 |
| Silane | 1.5 |
| Sulfur | 2 |
| MBTS | 1.0 |
| MBT | 0.2 |
| TMTM | 0.15 |
| Crosslinker from Example 1 | 2.5 |

The commercial sources of the components of the shoe sole formulations of Table 8 are as follows: cis-butadiene rubber: Budene 1207 from Goodyear Corporation; natural rubber: (SMR-L); nitrile rubber: Perbunan NT 2445 form Bayer; silica: HiSil 233 form PPG; diethylene glycol from Dow Corporation; BHT: butylated hydroxytoluene from Asia Pacific; ZnO: Kadox 720C from ZincCorp.; stearic acid: Industrene R from Witco, Crompton; wax: Sunolite 240 from Witco Corporation; activator: Rhenofit 2555 from Rhein-Chemie; dispenser: Aflux 12 from Rhein-Chemie;homogenizer: Phenosin N260 from Rhein-Chemie; sulfur: Rhenogran S-80 from Rhein-Chemie; MBTS: Thiofide from Flexsys; MBT: Thiotax MBT from Flexsys; TMTM: Rhenogran TMTM form Rhein-Chemie; silane: Silquest A-1289 silane from Momentive Performance Materials.

Other embodiments of the invention will be apparent to those skilled in the art from a consideration of this specification or practice of the invention disclosed herein. It is intended that the specification and examples be considered as exemplary only, with the true scope and spirit of the invention being defined by the following claims.

The invention claimed is:

1. A sulfur-containing cycloaliphatic compound of the general formula:

$$G[-C_aH_{2a}-S-S(=O)_b-R]_n \quad (1)$$

wherein G is a saturated, monocyclic aliphatic group of valence n containing from 5 to 12 carbon atoms and optionally containing at least one halogen or a saturated monocyclic silicone [RSiO—]$_n$[R$_2$SiO—]$_p$ group of valence n;

each R independently is a monovalent hydrocarbon of up to 20 carbon atoms; each occurrence of subscripts a and b independently is an integer wherein a is 2 to 6 and b is 1 or 2; n is an integer of from 3 to 6; and p is an integer of from 0 to 3.

2. The sulfur-containing cycloaliphatic compound of claim 1 wherein G is a cyclopentane, cyclohexane or cycloheptane group, optionally containing at least one chlorine.

3. A mixture of stereoisomers of the sulfur-containing cycloaliphatic compound of claim 1 wherein at least 50 weight percent of the mixture is isomer in which the —S—S(=O)$_b$—R groups are in the equatorial position relative to group G.

4. The sulfur-containing cycloaliphatic compound of claim 1 wherein each R independently is selected from the group consisting of methyl, ethyl, propyl, isopropyl, butyl, 2-ethylhexyl, cyclohexyl, cyclopentyl, phenyl, benzyl, tolyl, xylyl and methylbenzyl.

5. A sulfur containing cycloaliphatic compound comprising at least one member of the group consisting of:
methanethiosulfonic acid 2-[4,6-bis-(2-methanesulfonylsulfanyl-ethyl)-2,4,6-trimethyl-[1,3,5,2,4,6-]trioxatrisilinan-2-yl]-ethyl ester; benzenethiosulfonic acid 2-[4,6-bis-(2-benzenesulfonylsulfanyl-ethyl)-2,4,6-trimethyl-[1,3,5,2,4,6-]trioxatrisilinan-2-yl]-ethyl ester, toluenethiosulfonic acid 2-[4,6-bis-(2-toluenesulfonylsulfanyl-ethyl)-2,4,6-trimethyl-[1,3,5,2,4,6]trioxatrisilinan-2-yl]-ethyl ester, toluene-4-thiosulfonic acid S-{2-[bis-2,4-(2-toluene-4-sulfonylsulfanyl-ethyl)-cyclohexyl]-ethyl}ester, ethenethiosulfonic acid S-{2-[bis-2,4-(2-ethenesulfonylsulfanyl-ethyl)-cyclohexyl]-ethyl}ester, cyclohexanethiosulfonic acid S-{2-[bis-2,4-(2-cyclohexanesulfonylsulfanyl-ethyl)-cyclohexyl]-ethyl}ester, benzenethiosulfonic acid S-{2-[bis-2,4-(2-benzenesulfonylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, methanethiosulfonic acid S-{2-[bis-2,4-(2-methanesulfonylsulfanyl-ethyl)-2,4-dichloro-cyclohexyl]-ethyl}ester, methanethiosulfonic acid S-{2-[bis-2,4-(2-methanesulfonylsulfanyl-ethyl)-cyclopentyl]-ethyl}ester, methanethiosulfonic acid S-{2-[bis-2,4-(2-methanesulfonylsulfanyl-ethyl)-cycloheptyl]-ethyl}ester, methanethiosulfonic acid S-{2-[bis-2,4-(2-methanesulfonylsulfanyl-ethyl)-cyclododecyl]-ethyl}ester, toluene-4-thiosulfonic acid S-{2-[bis-2,4-(2-toluene-4-sulfonylsulfanyl-ethyl)-cyclooctyl]-ethyl}ester, toluene-4-thiosulfonic acid S-{2-[tris -2,4,6-(2-toluene-4-sulfonylsulfanyl-ethyl)-cyclooctyl]-ethyl}ester, toluene-4-thiosulfonic acid S-{2-[tetra-3,5,7,9-(2-toluene-4-sulfonylsulfanyl-ethyl)-cyclodecyl]-ethyl}ester, toluene-4-thiosulfonic acid S-{3-[bis-2,4-(2-toluene-4-sulfonylsulfanyl-propyl)-cyclohexyl]-ethyl}ester, toluene-4-thiosulfonic acid S-{4-[bis-2,4-(2-toluene-4-sulfonylsulfanyl-ethyl) -cyclohexyl]-butyl}ester, toluene-4-thiosulfonic acid S-{6-[bis-2,4-(2-toluene-4-sulfonylsulfanyl -ethyl)-cyclohexyl]-hexyl}ester, toluene-4-thiosulfinic acid S-{2-[bis-2,4-(2-toluene-4-sulfinylsulfanyl-ethyl)-cyclohexyl]-ethyl}ester, methylthiosulfinic acid S-{2-[bis-2,4-(2-methylsulfinylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, a mixture comprising 80 weight percent of toluene-4-thiosulfonic acid S-{2-[cis,cis-bis-2,4-(2-toluene-4-sulfonylsulfanyl-ethyl) -cyclohexyl]-ethyl}ester and at least 5 weight percent of toluene-4-thiosulfonic acid S-{2-[cis,trans-bis-2,4-(2-toluene-4-sulfonylsulfanyl-ethyl)-cyclohexyl]-ethyl}ester, and a mixture comprising of 85 weight percent of toluene-4-thiosulfonic acid S-{2-[cis,cis-bis-2,4-(2-toluene-4-sulfonylsulfanyl-ethyl)-cyclohexyl]-ethyl}ester and at least 5 weight percent of toluene-4-thiosulfonic acid S-{2-[trans,cis-bis-2,4-(2-toluene-4-sulfonylsulfanyl-ethyl) -cyclohexyl]-ethyl}ester.

6. A process for preparing the sulfur-containing cycloaliphatic compound of claim 1, and mixtures thereof, which comprises:
a) reacting poly-alkenyl-substituted cycloalkane with thioacid in the presence of a free-radical source to provide poly-thiocarboxylate-substituted alkylcycloalkane;
b) reacting poly-thiocarboxylate-substituted alkylcylcoalkane with deblocking agent to form free poly-mercaptan-functional alkylcycloalkane;
c) reacting free poly-mercaptan-functional alkylcycloalkane with halogenating agent to provide poly-sulfenyl halide-functional alkylcycloalkane; and,
d) reacting poly-sulfenyl halide-functional alkylcycloalkane with alkali metal salt of R—S(=O)$_b$⁻M⁺, wherein R is a monovalent hydrocarbon of up to 20 carbon atoms; M⁺ is a alkali metal cation; and the subscript b is 1 or 2, to yield the sulfur-containing cycloaliphatic compound.

7. A filled sulfur-vulcanizable elastomer composition which comprises:
(i) at least one sulfur-vulcanizable elastomer;
(ii) at least one particulate filler; and,
(iii) a crosslinking effective amount of, as crosslinker for sulfur-vulcanizable elastomer (i), at least one sulfur-containing cycloaliphatic compound of claim 1.

8. The filled sulfur-vulcanizable elastomer composition of claim 7 wherein sulfur-vulcanizable elastomer (i) is at least one member selected from the group consisting of cis-1,4-polyisoprene rubber, emulsion polymerization-prepared styrene/butadiene copolymer rubber, organic solution polymerization-prepared styrene/butadiene rubber, 3,4-polyisoprene rubber, isoprene/butadiene rubber,styrene/isoprene/butadiene terpolymer rubber, cis-1,4-polybutadiene rubber, medium vinyl polybutadiene rubber, high vinyl polybutadiene rubber, styrene/isoprene copolymer, emulsion polymerization-prepared styrene/butadiene/acrylonitrile terpolymer rubber, butadiene/acrylonitrile copolymer rubber emulsion polymerization-derived styrene/butadiene (ESBR) having a styrene content of from 20 to 28 percent bound styrene, and an ESBR having a bound styrene content of from 30 to 45 percent.

9. The filled sulfur-vulcanizable elastomer composition of claim 7 wherein particulate filler (ii) is at least one member selected from the group consisting of inert porous filler for carrying silane and filler that is reactive for silane, the filler being combined with at least one silane possessing functionality that is reactive for sulfur-vulcanizable elastomer (i).

10. The sulfur-vulcanizable filled elastomer composition of claim 9 in which the inert porous filler is carbon and the filler that is reactive for silane is silica.

11. The filled sulfur-vulcanizable elastomer of claim 9 in which the silane is a silylated core polysulfide.

12. The filled sulfur-vulcanizable elastomer of claim 10 in which the silane is a silylated core polysulfide.

13. The filled sulfur-vulcanizable elastomer composition of claim 7 wherein in sulfur-containing cycloaliphatic compound (iii), G is a cyclopentane, cyclohexane or cycloheptane group, optionally containing at least one chlorine.

14. The filled sulfur-vulcanizable elastomer composition of claim 7 wherein sulfur-containing cycloaliphatic compound (iii) is a mixture of steroisomers wherein at least 50 weight percent of the mixture is isomer in which the —S—S(=O)$_b$—R groups are in the equatorial position relative to group G.

15. The filled sulfur-vulcanizable elastomer composition of claim 7 wherein in sulfur-containing cycloaliphatic compound (iii), each R independently is selected from the group consisting of methyl, ethyl, propyl, isopropyl, butyl, 2-ethylhexyl, cyclohexyl, cyclopentyl, phenyl, benzyl, tolyl, xylyl and methylbenzyl.

16. A filled sulfur-vulcanized elastomer composition which comprises:
(i) at least one sulfur-vulcanizable elastomer;
(ii) at least one pariculate filler; and,
(iii) a crosslinking effective amount of, as crosslinker for sulfur-vulcanizable elastomer (i), at least one sulfur-containing cycloaliphatic compound, wherein sulfur-containing cycloaliphatic compound (iii) is at least one member of the group consisting of methanethiosulfonic acid 2-[4,6-bis-(2-methanesulfonylsulfanyl-ethyl)-2,4,6-trimethyl -[1,3,5,2,4,6]trioxatrisilinan-2-yl]-ethyl ester; benzenethiosulfonic acid 2-[4,6-bis-(2-benzenesulfonylsulfanyl-ethyl)-2,4,6-trimethyl-[1,3,5,2,4,6-]trioxatrisilinan-2-yl]-ethyl ester, toluenethiosulfonic acid 2-[4,6-bis-(2-toluenesulfonylsulfanyl-ethyl)-2,4,6-trimethyl-[1,3,5,2,4,6-]trioxatrisilinan-2-yl]-ethyl ester, toluene-4-thiosulfonic acid S-{2-[bis-2,4-(2-toluene-4-sulfonylsulfanyl-ethyl)-cyclohexyl]-ethyl}ester, ethenethiosulfonic acid S-{2-[bis-2,4-(2-ethenesulfonylsulfanyl-ethyl)-cyclohexyl]-ethyl}ester, cyclohexanethiosulfonic acid S-{2-[bis-2,4-(2-cyclohexanesulfonylsulfanyl-ethyl)-cyclohexyl]-ethyl}ester, benzenethiosulfonic acid S-{2-[bis-2,4-(2-benzenesulfonylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, methanethiosulfonic acid S-{2-[bis-2,4-(2-methanesulfonylsulfanyl-ethyl) -2,4-dichloro-cyclohexyl]-ethyl}ester, methanethiosulfonic acid S-{2-[bis-2,4-(2-methanesulfonylsulfanyl-ethyl) -cyclopentyl]-ethyl}ester, methanethiosulfonic acid S-{2-[bis-2,4-(2-methanesulfonylsulfanyl-ethyl)-cycloheptyl]-ethyl}ester, methanethiosulfonic acid S-{2-[bis-2,4-(2-methanesulfonylsulfanyl-ethyl)-cyclododecyl]-ethyl}ester, toluene-4-thiosulfonic acid S-{2-[bis-2,4-(2-toluene-4-sulfonylsulfanyl-ethyl)-cyclooctyl]-ethyl}ester, toluene-4-thiosulfonic acid S-{2-[tris -2,4, 6-(2-toluene-4-sulfonylsulfanyl-ethyl)-cyclooctyl]-ethyl}ester, toluene-4-thiosulfonic acid S-{2-[tetra-3,5, 7,9-(2-toluene-4-sulfonylsulfanyl-ethyl) -cyclodecyl]-ethyl1}ester, toluene-4-thiosulfonic acid S-{3-[bis-2,4-(2-toluene-4-sulfonylsulfanyl-propyl) -cyclohexyl]-ethyl}ester, toluene-4-thiosulfonic acid S-{4-[bis-2,4-(2-toluene-4-sulfonylsulfanyl-ethyl) -cyclohexyl]-butyl}ester, toluene-4-thiosulfonic acid S-{6-[bis-2,4-(2-toluene-4-sulfonylsulfanyl-ethyl)-cyclohexyl]-hexyl}ester, toluene-4-thiosulfinic acid S -{2-[bis-2,4-(2-toluene-4-sulfinylsulfanyl-ethyl)-cyclohexyl]-ethyl}ester,methylthiosulfinic acid S-{2-[bis-2,4-(2-methylsulfinylsulfanyl-ethyl)-cyclohexyl]-ethyl}ester, toluene-4-thiosulfonic acid S-{2-[bis-2,4-(2-toluene-4-sulfonylsulfanyl-ethyl)-cyclohexyl]-ethyl}ester, a mixture comprising 80 weight percent of toluene-4-thiosulfonic acid S-{2-[cis,cis-bis-2,4-(2-toluene-4-sulfonylsulfanyl-ethyl) -cyclohexyl]-ethyl}ester and at least 5 weight percent of toluene-4-thiosulfonic acid S-{2-[cis,trans-bis-2,4-(2-toluene-4-sulfonylsulfanyl-ethyl)-cyclohexyl]-ethyl}ester, and a mixture comprising of 85 weight percent of toluene-4-thiosulfonic acid S-{2-[cis,cis-bis-2,4-(2-toluene-4-sulfonylsulfanyl-ethyl)-cyclohexyl]-ethyl}ester and at least 5 weight percent of toluene-4-thiosulfonic acid S-{2-[trans,cis-bis-2,4-(2-toluene-4-sulfonylsulfanyl-ethyl)-cyclohexyl]-ethyl}ester.

17. The cured composition of claim 7.

18. The cured composition of claim 17 provided as a weather stripping, hose, belt, seal, gasket or shoe sole.

* * * * *